United States Patent
Abdulhalim

(10) Patent No.: US 10,151,634 B2
(45) Date of Patent: Dec. 11, 2018

(54) MULTI-SPECTRAL POLARIMETRIC VARIABLE OPTICAL DEVICE AND IMAGER

(71) Applicant: Ibrahim Abdulhalim, Wahat-Alsalam-Neve Shalom (IL)

(72) Inventor: Ibrahim Abdulhalim, Wahat-Alsalam-Neve Shalom (IL)

(*) Notice: Subject to any disclaimer, the term of this patent is extended or adjusted under 35 U.S.C. 154(b) by 0 days.

(21) Appl. No.: 15/527,098

(22) PCT Filed: Nov. 11, 2015

(86) PCT No.: PCT/IL2015/051092
§ 371 (c)(1),
(2) Date: May 16, 2017

(87) PCT Pub. No.: WO2016/075694
PCT Pub. Date: May 19, 2016

(65) Prior Publication Data
US 2017/0363472 A1  Dec. 21, 2017

Related U.S. Application Data

(60) Provisional application No. 62/080,336, filed on Nov. 16, 2014.

(51) Int. Cl.
*G01N 21/00* (2006.01)
*G01J 3/447* (2006.01)
(Continued)

(52) U.S. Cl.
CPC ............ *G01J 3/447* (2013.01); *G01J 3/26* (2013.01); *G01J 3/2823* (2013.01);
(Continued)

(58) Field of Classification Search
CPC ........ G01J 3/26; G01J 3/02; G01J 3/51; G01J 9/00; G01N 21/255
(Continued)

(56) References Cited

U.S. PATENT DOCUMENTS 5,381,253 A   1/1995  Sharp et al.
5,900,942 A   5/1999  Spiering
(Continued)

FOREIGN PATENT DOCUMENTS

WO   2008108846 A1   9/2008
WO   2013160890 A1   10/2013

OTHER PUBLICATIONS

Abdulhalim I, "Non-display bio-optic applications of liquid crystals", Liquid Crystals Today, pp. 44-60, vol. 20, No. 2 (Mar. 2011).
(Continued)

*Primary Examiner* — Md M Rahman
(74) *Attorney, Agent, or Firm* — The Roy Gross Law Firm, LLC; Roy Gross

(57) ABSTRACT

A system is described that combines spectropolarimetry with scatterometry. The system uses an annular mirror and liquid crystal devices to control the angle of the incident light cone, the polarization and wavelength, an imaging setup and one or more video cameras so that spectroseopic-polarimetric-scatterometric images can be grabbed rapidly. The system is also designed to incorporate additional imaging modes such as interference, phase contrast, fluorescence and Raman spectropolarimetric imaging.

11 Claims, 16 Drawing Sheets

(51) Int. Cl.
  *G01N 21/21*   (2006.01)
  *G01N 21/47*   (2006.01)
  *G02B 27/28*   (2006.01)
  *G02F 1/1347*  (2006.01)
  *G01J 3/28*    (2006.01)
  *G01J 3/44*    (2006.01)
  *G01J 3/45*    (2006.01)
  *G02F 1/139*   (2006.01)
  *G01J 3/26*    (2006.01)
  *G01J 4/00*    (2006.01)
  *G01N 21/64*   (2006.01)
  *G01N 21/65*   (2006.01)
  *G01N 21/84*   (2006.01)
  *G01J 3/12*    (2006.01)

(52) U.S. Cl.
  CPC ............... *G01J 3/4412* (2013.01); *G01J 3/45* (2013.01); *G01J 4/00* (2013.01); *G01N 21/21* (2013.01); *G01N 21/4738* (2013.01); *G02B 27/286* (2013.01); *G02F 1/1393* (2013.01); *G02F 1/13471* (2013.01); *G01B 2210/56* (2013.01); *G01J 2003/1269* (2013.01); *G01J 2003/2826* (2013.01); *G01J 2003/451* (2013.01); *G01N 21/64* (2013.01); *G01N 21/65* (2013.01); *G01N 21/8422* (2013.01); *G02F 2203/055* (2013.01); *G02F 2203/12* (2013.01)

(58) Field of Classification Search
  USPC ............................................. 356/73
  See application file for complete search history.

(56) References Cited

U.S. PATENT DOCUMENTS

| | | |
|---|---|---|
| 6,273,571 B1 | 8/2001 | Sharp et al. |
| 6,522,469 B1 | 2/2003 | Fuqua et al. |
| 6,545,739 B1 | 4/2003 | Matsumoto et al. |
| 2009/0284708 A1 | 11/2009 | Abdullhaim |
| 2009/0309960 A1 | 12/2009 | Park et al. |
| 2011/0279744 A1 | 11/2011 | Voigt et al. |
| 2012/0300143 A1 | 11/2012 | Voigt et al. |
| 2014/0098309 A1 | 4/2014 | Shi |
| 2017/0059299 A1* | 3/2017 | Safrani .................. G02B 27/10 |

OTHER PUBLICATIONS

Solodar et al, "Annular liquid crystal spatial light modulator for beam shaping and extended depth of focus" Optics Communications, pp. 167-173, vol. 323, (Feb. 2014).

Kundikova et al.,"Tunable quarter-wave plate for determining light wavelength", Technical Physics Letters, pp. 63-66, vol. 35, No. 1 (Jan. 2009) abstract.

* cited by examiner

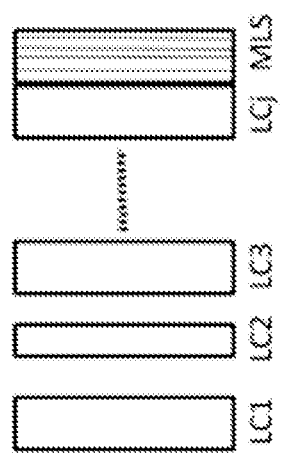
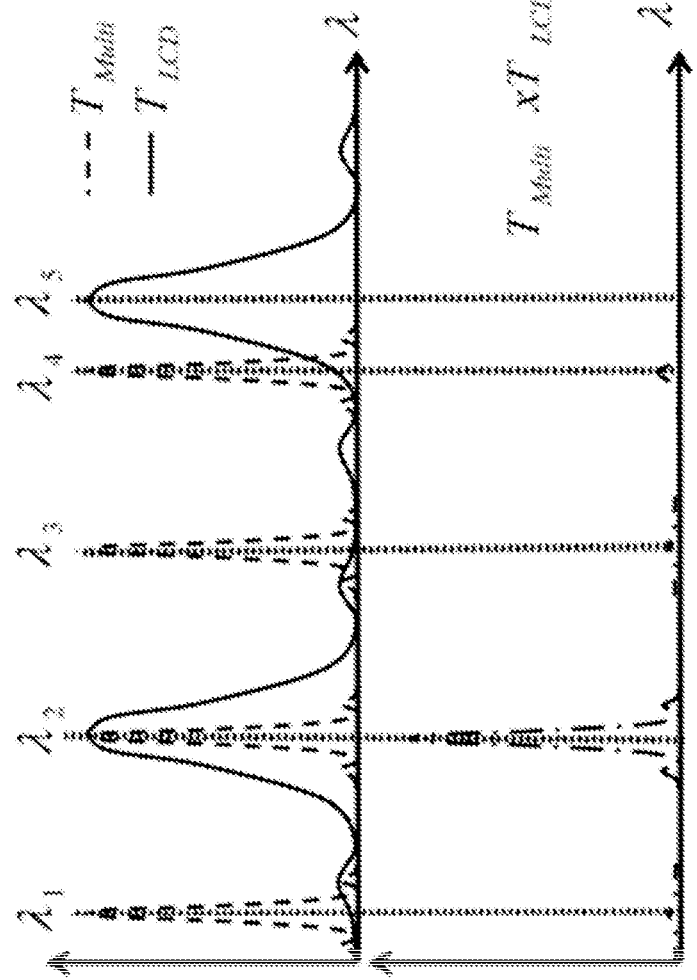
Fig. 1a
Fig. 1b
Fig. 1c

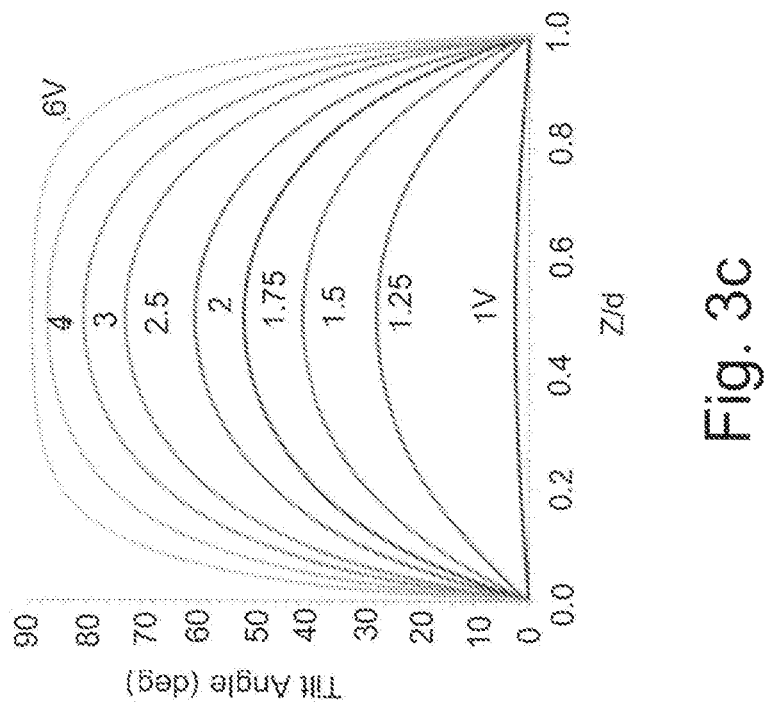
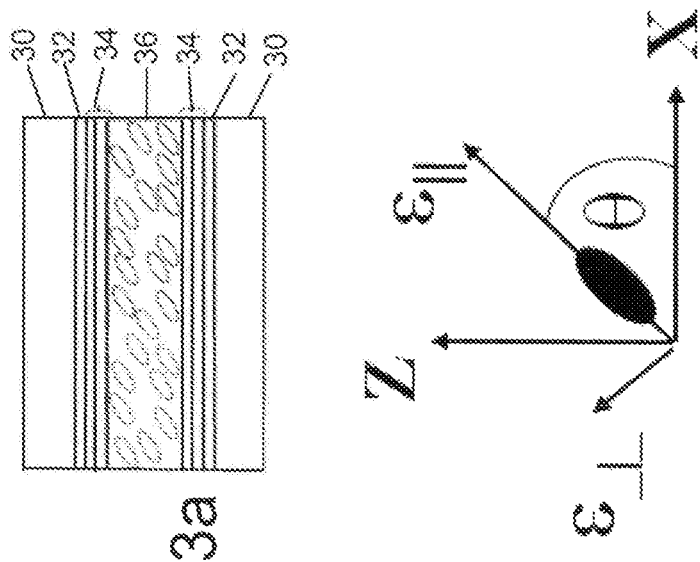
Fig. 3a  Fig. 3b  Fig. 3c

MULTI-SPECTRAL POLARIMETRIC VARIABLE OPTICAL DEVICE AND IMAGER

FIELD OF THE INVENTION

The invention is from the field of optics. Specifically the invention relates to devices and methods for diagnostics and inspection using narrow spectral bands of the illuminating light and many polarization orientations.

BACKGROUND OF THE INVENTION

Publications and other reference materials referred to herein are numerically referenced in the following text and respectively grouped in the appended Bibliography which immediately precedes the claims.

In many biomedical diagnostics and industrial inspection methodologies there is a need for a number of separated narrow spectral bands of the illuminating light and several polarization orientations. This first methodology is called multispectral imaging or multispectral diagnostics technique. The second methodology is called polarimetric imaging. The combination of the two methodologies is called by the inventor multi-spectral polarimetric imaging (MSPI).

An important application of MSPI is in optical spectropolarimetric scatterometry (OSIS) where the object is scattering and the scattered light is monitored rather than the specular reflection. In the semiconductor industry, periodic patterns are produced on the wafer as marks for monitoring the fabrication process. One of the techniques being used to measure the parameters of this periodic structure is called optical scatterometry. Optical scatterometry is used in the inspection of the fabrication processes of optical surfaces because light scattered from the surface is an indication of the degree of roughness of the surface. One of the inventions on the subject was by the present inventor [1]. Since the sample is periodic, in these patents the diffracted beams are collected and measured versus the wavelength using a spectrometer, more specifically the zero order diffraction is collected. Two measurement modes were proposed, one that uses fixed polarizers, while the other uses a rotating polarizer in order to extract the ellipsometric parameters of the scattered light.

Another important application of MSPI is in the field of biomedical imaging. Bio-tissue is usually scattering with strong polarization and wavelength dependence. For example when linearly polarized light illuminates the skin, part of it is backscattered by dermal layers and rapidly depolarized by birefringent collagen fibers [2]. The birefringence produces phase retardation between light polarized along the collagen fibers and the light polarized perpendicular to their long axis. The properties of the scattered light are therefore polarization dependent and as the scattering increases the chances that a photon loses its original polarization state are high. As the photon penetrates deeper into the tissue it will experience more and more scattering events, hence the depolarization depends on the penetration depth. The penetration depth and amount of depolarization depends on the wavelength of the incident light. Hence, there is strong polarization and wavelength dependence of light polarized from the skin. It is possible to distinguish such backscattered light from the total diffusely reflected light that is dominated by light penetrating deeply into the dermis by means of the different polarimetric spectral imaging and polarized spectroscopy.

In order to apply the MSPI method to industrial and biological applications such as those described above it is necessary to employ a compact tunable element that can select each wavelength in a narrowband (<20 nm full width at half maximum (FWHM)) and fast speed (<30 msec) sequentially and to be able to control its polarization state.

Mechanisms of polarized light scattering from different tissues and tissue phantoms are well established now, based on in vitro studies. Parameters such as depolarization depth (DD), retardance, and birefringence have been studied both theoretically and experimentally. Polarized light traveling through different tissues (skin, muscle, and liver) depolarizes after a few hundred microns. Highly birefringent materials such as skin (DD=300 μm at 696 nm) and muscle (DD=370 μm at 696 nm) depolarizes light faster than less birefringent materials such as liver tissue (DD=700 μm at 696 nm).

In a simplified manner one can distinguish between two components of linearly polarized light scattered from the skin. The first, which maintains the polarization of the incident light, is the regular (specular) reflection that comes predominately from the surface of the skin. The second component undergoes multiple scattering from the various skin layers, and is therefore depolarized. Hence, using polarizers, one of the components can be eliminated, and consequently enhances either superficial topography (wrinkles, fine lines, pores) or subsurface structures (pigmentation, erythema, infiltrates, vessels) of the skin. The wavelength dependence of the DD provides another degree of freedom to modify and study. The research group of the present inventor has built a spectropolarimetric module that either uses two wavelengths with two polarization states or multiple incident linear polarizations at two different wavelengths [3,4,5,6]. However in that module the analyzer was fixed and the illumination was hitting the tissue asymmetrically.

It is therefore a purpose of the present invention to provide symmetric illumination, a compact tunable element that can select each wavelength in a narrowband and fast speed sequentially and to control its polarization state both in the input and at the output.

It is another purpose of the present invention to provide imaging apparatus that comprises the tunable element.

It is another purpose of the present invention to provide diagnostic and inspection methods of using the apparatus comprising the compact tunable element in industrial and biological applications.

Further purposes and advantages of this invention will appear as the description proceeds.

SUMMARY OF THE INVENTION

The invention is a powerful multi-spectral polarimetric variable optical device and imaging apparatus comprising the same device that can be utilized in many applications in biomedical diagnostics, biometric identification and industrial inspection. Various aspects and embodiments of the invention are based on the following novel features:

1. Using a combination of a small number of variable retardation liquid crystal (LC) devices integrated with periodic dielectric multilayered structure to give narrowband spectral output tunable using a small voltage.
2. Using a single LC variable retardation device combined with passive thin film anisotropic plates to continuously rotate the polarization plane of the selected narrowband light beam using a small voltage.
3. Using a wide field of view LC device made of even number of homogeneously aligned nematic LC devices wherein in each pair the two nematic LC devices are stacked together so that the LC molecules orientations in them are mirror images to each other.

4. The use of special voltage driving scheme to an even number of variable LC retarders (splayed ferroelectric structure with fixed boundary orientations or homogeneously aligned nematic) to make the retardation changing linearly with the voltage, so that Fourier or wavelet transforms processing can be used to yield the spectral information at the wavelengths of interest in parallel. The unit that contains the even number of LC devices oriented so that their optic axis is at 45 degrees to the polarizer axis and the special voltage driving is called by the inventor: "liquid crystal spectral modulation (LCSM) unit" and this configuration is called by the inventor the spectral modulation parallel approach (SMPA). It is different from the LC tunable filter (LCTF) in that it provides the spectral information on all the spectral bands in parallel rather than selecting each band in series. The LCSM unit can also be made of a combination of LC devices based on different modes stacked together between polarizers so that their output is modulated by the applied voltage and then processed to give the spectrum of the object.

5. Using a pixelated LC device to control the beam shape and its angular extent as well as the depth of field.

6. The use of achromatic tunable waveplate combination of one or more LC devices combined with additional anisotropic layers.

7. Design of a miniature imaging module that comprises the following novel features:
   a. Integrating features 1 and 2 (from this list) into the illumination path and locating them in a plane conjugate to the field plane so that uniformity of the wavelength and polarization over the whole field is obtained.
   b. Using an annular mirror to split the illuminating beam so that only an annulus of angles is directed towards the objective lens and illuminating the object symmetrically while letting the scattered light to pass through the central hole of the annular mirror towards a projecting lens and camera. The annular mirror has the additional advantage of preventing unwanted reflections from a beam splitter cube.
   c. Locating the pixelated LC device (feature 5 in this list) to control the annulus of the illuminating beam.
   d. Locating an additional polarization controller element similar to feature 2 in the imaging path together with a linear polarizer above the splitting mirror.
   e. Using a telecentric design in order to avoid magnification variation with defocus.
   f. The use of more than one camera with polarizer in front having different orientations to grab multiple polarimetric images simultaneously.
   g. The use of color masks in front of each camera or configuring different pixels of each camera to transmit only a single color each and combined with feature 6 in this list in order to grab multiple spectropolarimetric images in parallel.
   h. The use of a camera with polarization mask in front of the camera chip or configuring different pixels of the camera to transmit only a single polarization in order to grab multiple spectropolarimetric images in parallel.
   i. The use of feature 4 combined with feature 6 in features f or h in order to reveal fast spectropolarimetric images.

8. Methodology of how to grab images and process them to find the best images of a scattering medium with applications in the following areas:
   a. Biomedical imaging such as for retinal imaging and skin cancer diagnosis.
   b. Inspection of food freshness such as: freshness of meat, fish and other important products.
   c. Biometric identification.
   d. Remote sensing.

One embodiment of the methodology involves selecting an incident wavelength then a polarization state then scanning over many output polarization states, then repeating the process for all the wavelengths and incident polarization states. Processing of the different polarization images by subtraction and normalization will then reveal the images with best contrast. The first preference is for the set of images at which the input and output polarization rotators orientations are orthogonal to each other. In another methodology the Stokes images and even Mueller matrix images will be obtained.

In a first aspect the invention is a multi-spectral polarimetric variable optical device comprising a liquid crystal aperture tuning unit (LCTA), at least one liquid crystal polarization controller (LCPC) unit, and one of a liquid crystal tunable filter (LCTF) unit or a liquid crystal spectral modulation (LCSM) unit.

In embodiments of the multi-spectral polarimetric variable optical device of the invention the LCTA unit comprises an annular liquid crystal spatial light modulator.

In embodiments of the multi-spectral polarimetric variable optical device of the invention the LCTF unit comprises at least one liquid crystal (LC) switchable layer and a dielectric multilayered thin film stack deposited either on one of the external sides of one of the constituent LC layers or on a separate substrate, the LCTF unit having an output comprising a single narrow spectral band that is tunable by an external field. The external field can be one of the following: electrical, magnetic, optical, and thermal.

In these embodiments of the multi-spectral polarimetric variable optical device of the invention the multilayered thin film stack can be comprised of one of the following:
   a. alternating layers of low refractive index and high refractive index transparent dielectric materials with variable thicknesses in the stack;
   b. two stacks of alternating layers of low refractive index and high refractive index transparent dielectric materials with a defect layer between them;
   c. a mixture of isotropic and anisotropic layers;
   d. a subwavelength grating structure combined with isotropic layers;
   e. a guided mode resonance structure; and
   f. a Fabry-Perot type etalon with an LC material in the cavity;

and each of the LC switchable layers can be comprised of one of the following LC materials:
   a. uniformly aligned nematic;
   b. an assembly of even number of anti-parallel aligned nematic LC layers wherein each pair of layers has the same thickness and oriented as mirror images one to the other;
   c. twisted nematic;
   d. ferroelectric; and
   e. helical.

In embodiments of the multi-spectral polarimetric variable optical device of the invention the LCPC unit comprises one variable LC retarder and one or more passive anisotropic plates. In these embodiments the LCPC unit can operate as a polarization rotator. In these embodiments one of the passive anisotropic plates can be a subwavelength grating.

In embodiments of the multi-spectral polarimetric variable optical device of the invention comprising a liquid crystal spectral modulation (LCSM) unit the LCPC units can be replaced by tunable achromatic waveplates and a continuous voltage waveform is applied to the LCSM unit so that the retardation varies linearly with time and Fourier or wavelet transforms are applied to obtain all the spectral information at once. Alternatively the output spectrum of the LCSM is modulated at several voltage ranges and the output of all the ranges is processed to reconstruct the reflected or transmitted or scattered spectrum of the object. In this case other processing schemes are possible such as the Wiener matrix estimation approach.

In a second aspect the multi-spectral polarimetric variable optical device of the first aspect is configured as a multi-spectral polarimetric imaging system.

Embodiments of the multi-spectral polarimetric imaging system of the invention comprise the following elements:
 a. a light source;
 b. an aperture stop in front of the light source;
 c. a LCTA unit located immediately in front of the aperture stop;
 d. a first lens in front of the LCTA unit;
 e. a polarizer in front of the first lens;
 f. an LCTF unit or a LCSM unit in front of the polarizer;
 g. a field stop immediately in front of the LCTF unit;
 h. a first LCPC unit immediately in front of the field stop;
 i. a second lens in front of the first LCPC unit;
 j. an annular mirror oriented at 45 degrees to the light from the light source that passes through elements "b" to "i";
 k. a light trap that absorbs light from the light source that passes through the open center of the annular mirror;
 l. an objective lens that receives light reflected by the annular mirror;
 m. a window through which light focused by the objective lens passes;
 n. a sample on which the objective lens focuses the light;
 o. a second LCPC unit, which receives light that is reflected by or scattered from the surface of the sample and passes through the window, the objective lens, and the open center of the annular mirror;
 p. an analyzer in front of the second LCPC unit;
 q. a third lens in front of the analyzer; and
 r. a digital camera onto which the third lens focuses the light reflected or scattered from the surface of the sample.

In embodiments of the multi-spectral polarimetric imaging system of the invention elements "a" to "r" can be separated into several smaller units that can be reassembled in different ways to provide many different products for different applications.

In embodiments of the multi-spectral polarimetric imaging system of the invention the third lens (element "q") and the camera (element "r") are replaced by an adapter configured to fit the imaging module into a digital camera or cellular phone.

In embodiments of the multi-spectral polarimetric imaging system of the invention a built in zoom of the digital camera can be used to vary the magnification.

In embodiments of the multi-spectral polarimetric imaging system of the invention the annular mirror can be replaced with a regular beam splitter.

In embodiments of the multi-spectral polarimetric imaging system of the invention the analyzer and camera are replaced by at least one beam splitter placed after the third lens, wherein the beam splitters divide the light passing through the third lens into at least two channels each of which comprises an analyzer and a camera, wherein the orientation of each analyzer is different from the orientation of each of the others. In an embodiment the number of beam splitters is two and the number of analyzers and cameras is three. In these embodiments the LCTF unit can be replaced with a LCSM unit and each of the first and second LCPC units can be replaced with a tunable achromatic waveplate.

These embodiments of the multi-spectral polarimetric imaging system may comprise a color mask on a glass plate fitted on top of the digital cameras sensor chip, wherein the imaging system does not comprise a LCTF unit and each of the first and second LCPC units is replaced by two or more LC retarders oriented at different angles with respect to each other with different voltages applied to each of them to act as tunable achromatic waveplates.

Alternatively in these embodiments the imaging system does not comprise analyzers and does comprise a polarization mask on a glass plate fitted on top of the digital cameras sensor chip. In these embodiments the LCTF unit can be replaced with a LCSM unit and each of the first and second LCPC units can be replaced with a tunable achromatic waveplate. In this later embodiment the liquid crystal spectral modulation (LCSM) unit is placed in between the annular or regular beam splitter and the objective lens so that double pass is achieved.

In embodiments of the multi-spectral polarimetric imaging system of the invention the objective lens is replaced with an interferometric microscope objective and beam splitter, as in the Mirau or Michleson interferometer, or with two objectives, as in the Linnik interferometer, and the imaging system is configured to capture the interferometric images at different depths of the sample, different polarization states and different wavelengths.

Embodiments of the multi-spectral polarimetric imaging system of the invention can be used for medical diagnosis and monitoring, industrial process inspection, and remote sensing.

Embodiments of the multi-spectral polarimetric imaging system of the invention can be combined with a spectroscopic system, which can measure the scattering spectrum, Raman scattering, or fluorescence. In these embodiments once a small area in the sample is identified, higher magnification is applied and all or part of the scattered light is directed to the spectroscopic system.

All the above and other characteristics and advantages of the invention will be further understood through the following illustrative and non-limitative description of embodiments thereof, with reference to the appended drawings.

BRIEF DESCRIPTION OF THE DRAWINGS

FIG. 1a is a schematic drawing of a device of the invention showing the liquid crystals elements and the multilayer stack on one of the faces of the $j^{th}$ LC element;

FIG. 1b schematically shows an example for the transfer functions of the LCD and the multilayer stack of FIG. 1a;

FIG. 1c schematically shows the output spectrum as a result of the multiplication of the two transfer functions shown in FIG. 1b;

FIG. 3a schematically shows a uniformly aligned nematic LC device;

FIG. 3b schematically shows the molecular orientation and the principal values of the dielectric tensor of the molecules in the LC layer in FIG. 3a;

FIG. 3c contains graphs showing the profiles of the tilt angle in response to an applied voltage calculated for LC E44 of Merck at different voltages as indicated on the graphs;

DETAILED DESCRIPTION OF EMBODIMENTS OF THE INVENTION

The present invention is a system that combines spectropolarimetry with scatterometry. The system is called by the inventor an optical spectropolarimetric scatterometric imaging (OSIS) system. The system uses an annular mirror and liquid crystal devices to control the angle of the incident light cone, the polarization and wavelength, an imaging setup and one or more video cameras so that spectroscopic-polarimetric-scatterometric images can be grabbed rapidly. The system is also designed to incorporate additional imaging modes such as interference, phase contrast, fluorescence and Raman spectropolarimetric imaging.

Figure 3D:
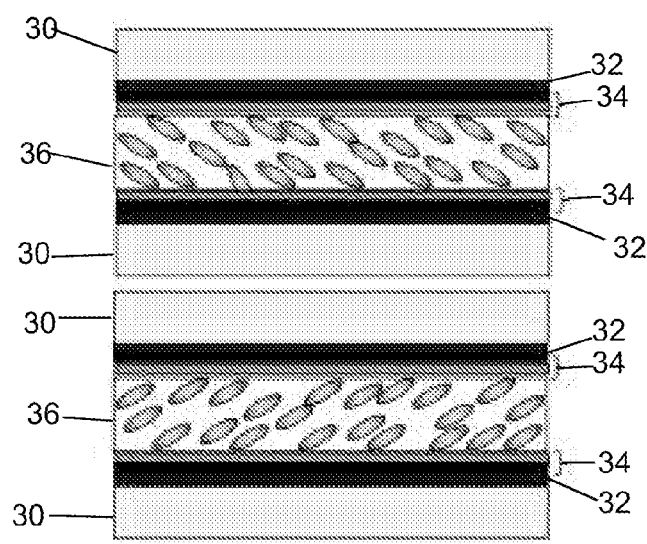
FIG. 3d schematically shows the arrangement of a pair of anti-parallel aligned LC devices having the same thickness but oriented so that their molecules directions are mirror images of each other.

Continuously tunable LC (liquid crystal) filters usually have one of the following disadvantages: (1) low speed, (2) limited dynamic range, (3) low light throughput, (3) narrow angular field and (4) wide spectral bandwidth. As the bandwidth narrows usually the light throughput and the speed degrade more. One of the methods of this invention to overcome these disadvantages while using LC filters to obtain polarization controlled narrow bandwidth, multispectral fast imaging involves the use of a fast tunable LC filter in a compact manner and with higher light throughput. The idea is based on the integration of a small number of LC devices combined with some passive multilayered thin film structures and anisotropic plates as well as color masks on or in front of the camera chip. The integration of these elements into a novel miniature imaging module is described herein below. The advantage of using a small number of LC devices is the high light throughput attainable and the ease of driving while the advantage of using multiple cameras and color masks on their chip speeds up more the grabbing of multiple spectropolarimetric images. The use of a polarization mask in front of the camera together with the tunable filter also speeds up the grabbing of multiple spectropolarimetric images. To overcome the narrow angular field of an anti-parallel aligned nematic LC device of thickness d, it is possible to use parallel aligned device (pi-cell) or vertically aligned device; however the invention discloses dividing the anti-parallel aligned device into an assembly of even number of thinner devices wherein each pair of devices in the assembly has the same thickness and each device in the pair is oriented so that the LC molecules orientations are mirror images of each other (see FIG. 3d). The breakage of the thick device into an assembly of even number of thinner ones has another advantage of making the whole device faster because the response time of the device increases with $d^2$. Other methods used in the LC displays industry for increasing the field of view can be implemented here as well such as the addition of anisotropic compensation plates.

The multimodal system of the invention combines the spectral polarimetric imaging module with polarized optical spectroscopy such as Raman [7], fluorescence [8] and diffuse reflectance [9] enabling the system to accentuate minute characteristics of many dermatological conditions, including filamentary structure, vascular lesions (such as portwine stains, rosacea and periungual telangiectasia), inflammatory lesions (such as psoriasis and acne), pigmented lesions (naevi and lentigines) and photodamaged skin. The idea is that following the SP imaging, a small area in the skin mole might be determined as suspicious of being cancerous, and so a zoom is applied on this area and the more detailed spectroscopic information (in addition to the multispectral one) from these units is grabbed for further analysis.

The method of the invention involves acquisition of two or more spectral images through an analyzing linear polarizer in front of the cameras and then performing image processing operations. Scattered light is usually partially polarized, characterized by the four Stokes parameters: $S=(S_0, S_1, S_2, S_3)$. More detailed information can be obtained by measuring the Mueller matrix M which connects the input and output Stokes parameters $S_{out}=MS_{in}$.

The present invention resolves several important problems of the prior art spectropolarimetric module built by the inventors research group to distinguish between two components of linearly polarized light scattered from the skin.

These problems are overcome by: (i) symmetric illumination which overcomes the problems of shadowing and light beam nonuniformity, (ii) full polarimetric imaging by incorporating polarization control element in the output in addition to the one in the input, (iii) telecentric design which gives possibility to change the focus without affecting the magnification and the symmetry of the image, (iv) the use of many wavelengths gives more information on the chromophores which gives spectral signatures of the specific tissue cancer, (v) the use of multiple incidence angles gives another degree of freedom in selecting the best illumination cone and grabbing images at different illumination cones which reveal scattered light from different depths in the tissue, (vi) an additional novel parallel detection scheme using multiple camera with analyzers in front oriented differently and the use of color masks on each camera chip combined with the use of liquid crystal achromatic waveplates, (vii) the use of polarization mask on the camera chip together with the use of the tunable filter, (viii) the spectral modulation parallel approach (SMPA) described herein below, (ix) the use of LC devices with improved angular field of view and (x) more comprehensive analysis of the images. The masking of the cameras with a wavelength mask, avoids the use of tunable spectral filters, thus making the image grabbing faster and the system more compact. The invention also discloses multimodal system in which a full scattered spectrum, fluorescence or Raman scattering measurements can be done in parallel to the spectropolarimetric images.

Figure 2:
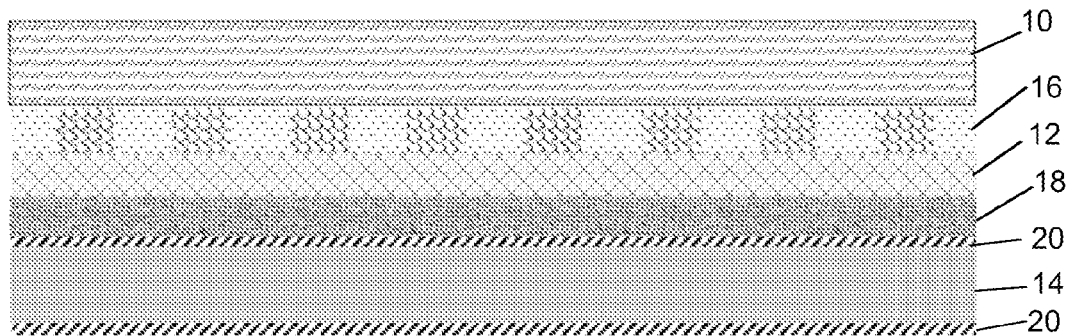
FIG. 2 schematically shows an embodiment of a guided mode resonant structure with a superstrate layer thick enough to reveal a series of narrow spectral peaks in reflection.

The multi-spectral tunable filtering concept of the invention is based on integrating a multilayered subwavelength structure on a single substrate which could be an integrated part of the LCD as shown in FIG. 1a, which is a schematic drawing of a device of the invention showing the liquid crystals elements and the multilayer stack on one of the faces of the jth LC element. Due to interference effects the output of the filter is a single narrow spectral band centered at the wavelength $\lambda$. Without the additional multilayered stack the transfer function, i.e. output $T_{LCD}(\lambda)$, of the LCD is a series of wide spectral bands such as shown in FIG. 2b or a single wide spectral band. On the other hand without the LCD the multilayered stack output consists of a series of N narrow spectral bands is $$T_{Multi}(\lambda) = \sum_{j=1}^{N} T_j(\lambda_j).$$

The end result of combining the two elements is the output function: $T_{out}(\lambda) = T_{LCD}(\lambda) T_{Multi}(\lambda)$ which should give a single narrow band given by the crossing of the two functions: $T_{LCD}(\lambda) \cap T_{multi}(\lambda)$ as shown in FIG. 1c. The output peak can be tunable by applying an external field to the LCD element. Note that in FIG. 1b the peak at $\lambda_5$ is outside the range of interest and therefore it does not affect the device performance. The peak at $\lambda_5$ can be removed completely by inserting a short pass edge filter. The difference from a Fabry-Perot type tunable LC filter should be clarified in which the two substrates are coated with mirrors but in the present invention only one substrate of at least one of the LCDs is coated with a stack of multilayered thin films that does not act as a mirror but as a passive multispectral narrowband filter. Materials from which the multilayered stack can be made are transparent dielectric materials such as the low refractive index materials $MgF_2$, $SiO_2$, combined with the high index materials such as $TiO_2$, or $Ta_2O_5$ and $Si_3N_4$. The design of standard dielectric mirrors, comprising a stack of alternating high and low index materials with refractive index ratio higher than or close to 2, usually gives high reflectivity over wideband spectrum. One proposition in this invention is then to use two such stacks with a defect layer in between. For example to get 10 wavelengths in the visible and near infrared range 400-1000 nm, the defect layer can be made of SiO2 with thickness around 1-2 microns. Other variations of this proposition are possible such as the use of quasiperiodic stack. More possibilities are described in the next section.

In another embodiment, the stack can be standing alone on a separate substrate. Since the optical properties of LCs change upon applying an external force on them (for example heating, electric, magnetic or optical fields) the output peak wavelength $\lambda$ shifts with the application of the external field. The preferable embodiment of the invention uses an electric field however thermal heating and in certain cases magnetic fields are also desirable. The most preferable embodiments of the filter comprise:

1. Single nematic LCD and a dielectric stack.
2. At least one pair of LCDs where each pair consists of two aligned LCDs assembled together so that their molecule directors are mirror images of each other and the whole assembly is combined with a dielectric stack on one of its surfaces.
3. Single ferroelectric LCD and a dielectric stack.
4. Single helical LCD operating in reflection and a dielectric stack.
5. Several LCD components combined with one of the configurations in 1, 2 or 3.

The Dielectric Stack as a Source of a Series of Narrow Spectral Bands:

A series of separated narrow spectral bands (<20 nm FWHM) can be achieved in several standard methodologies such as: a combination of laser diodes (LDs), a combination of light emitting diodes (LEDs), a Fabry-Perot etalon, and a combination of several passive filters. The present invention is able to achieve this result using a single multilayered stack deposited on one side of a solid substrate. The filter of the invention can also be used to give narrower spectral bands than those given by LEDs, by combining it with a multiple LED source. The advantages of this embodiment are for compactness and their ease of fabrication with large surface areas and with high quality. The transfer function of such a stack can be treated using the Abeles 2×2 characteristic matrix approach if all the layers are isotropic or using the 4×4 propagation matrix approach developed by the inventor when part or all the layers are anisotropic [10].

As an example consider the following one dimensional photonic crystal structure with a defect layer C in between: $(AB)^{N_p}(C)(AB)^{N_p}$. The layers of materials A, B and C and their thicknesses can be chosen to give an output that consists of a series of narrow spectral bands in the spectral region of interest. For this purpose the optical thicknesses of the A and B layers preferably have thicknesses $d_{A,B}$ equal to a quarter wavelength: $d_{A,B} = \lambda_c / 4n_{A,B}$ with $\lambda_c$ being the center wavelength of the spectral region of interest and $n_{A,B}$ are the corresponding refractive indices. The number of periods $N_p$ and the thickness and refractive index of layer C are then used to optimize the number of separate narrow bands and their FWHM. The spectral range and also the angular range can be widened by having a large contrast between the two refractive indices $n_{A,B}$. For example the ratio $n_A/n_B \geq 2$ will give very narrow spectral bands over very wide angular and spectral ranges. The stack $(AB)^{N_p}$ does not need to be a periodic stack and it can also be quasi periodic for example the following Fibonacci sequence which is based on the recursive relation $S_{j+1}=\{S_{j-1}, S_j\}$ for $S_0=\{B\}$, $j\geq 1$ $S_1=\{A\}$, $S_2=\{BA\}$, $S_3=\{ABA\}$, $S_4=\{BAABA\}$. The required multi-layered stack may then be written as: $(S_j)^{N_p}(C)(S_j)^{N_p}$ with $S_j$ being one of the sequences of Fibonacci. Other periodic structures or quasiperiodic sequences or their combinations are also possible and the invention is not limited to the two-layer periodic case or to the Fibonacci sequence case. To widen even further the spectral band of the mirror, the thicknesses of the layers can be changed slightly and nearly randomly around their nominal value. For example consider a two layer unit cell of: $\{A,B\}=\{MgF_2, TiO_2\}$ repeated 6 times on a BK7 glass substrate with the following thicknesses in nm: $M_1=\{\{40,30\}, \{108,40\}, \{121,49\}, \{152,71\}, \{149,80\}, \{181,89\}\}$ then a stack such as: $M_1/Ta_2O_5$ (790 nm)/$M_1$ gives a series of 10 transmission peaks in the range 400-1100 nm. Variations on this structure are also possible, for example increasing the number of unit cells increases the reflectivity further and increasing the thickness of the layer $Ta_2O_5$ increases the number of transmission peaks even further.

Another embodiment is the use of a mixture of isotropic and anisotropic multilayers. Anisotropic multilayers could be deposited with the glancing angle deposition technique. Using this technique one can manufacture thin solid films with high birefringence and transparency. An example of such structure operating in reflection is the stack of anisotropic alternating dielectric layers at wavelengths near the edge of the photonic band gap where it acts as an omnidirectional mirror proposed by the present inventor [11].

Another embodiment for the multilayered stack is the use of subwavelength grating structures combined with isotropic layers. For example wire grid polarizers WGP are known to reflect one of the polarizations (TE) over wideband and transmit the other polarization (TM). Hence stacking two WGPs with the grating lines parallel to each other with a gap in between gives a series of transmission TM polarized narrow peaks. Another example of structure that can act as such a multilayered stack is called guided mode resonance (GMR) structure shown in FIG. 2, in which one can get more than one resonant peak in reflection by adjusting the thickness of the top superstrate layer 10. To operate the device in reflection the preferred embodiment is to direct the incident beam on the GMR structure at small incidence angle and then let the reflected beam pass through the LCD.

Alternatively normal incidence is also possible with the addition of a beam splitter. Example of materials of the layers and their dimensions are: $Si_3N_4$ for the waveguide layer 12 of thickness in the range 300-800 nm, substrate 14 is glass such as fused silica and the grating 16 is $Si_3N_4/SiO_2$ of height in the range 50-200 nm and period in the range 300-400 nm in order to obtain the multiple resonances in the range 450-1000 nm. Layer 18 is a buffer layer and layers 20 are antireflection coating layers. The light is incident from air and the superstrate layer is made of a material having refractive index around 1.6 and thickness of few microns or more.

Another embodiment of a structure that can provide the series of discrete transmission peaks is a Fabry Perot (FP) type etalon since its transmission function consists of a series of transmission peaks that can be designed by choosing the correct parameters of the mirrors and the thickness and refractive index of the cavity medium. The output of an FP etalon depends strongly on the uniformity of the cavity thickness and therefore, although it is possible, it is a less preferred embodiment. However an advantageous FP etalon will be one containing a LC material in the cavity which can tune the FP resonances using a small voltage and provide another degree of freedom to adjust the transmission peak to get the maximum transmission at the desired wavelength. The dielectric stack in FIG. 3a can be thought of as the FP broadband mirrors with an alignment layer on top and the transparent conducting oxide (TCO) layer on the bottom wherein the gap is filled with a liquid crystal.

The LCD as a Spectral Modulator and as a Source of a Series of Wide Spectral Bands:

Case 1: Single Nematic LCD:

The switching properties of uniformly aligned nematic LCs depend strongly on the anchoring of the molecules at the surfaces. For example if the molecules long axes on the substrates are parallel to each other (in what is called pi cell) the device speed is faster than the case when they are anti-parallel. The vertically aligned mode is obtained when the molecules long axis is perpendicular to the substrates and the LC material has negative dielectric anisotropy. In a twisted nematic LC the molecules axes on the two substrates are oriented at different azimuths resulting in a twisted non uniform structure even at zero field.

FIG. 3a schematically shows a uniformly aligned nematic LC device. In the figure are seen glass layers 30, transparent conducting oxide layers 32, dielectric layers 34, and liquid crystal layer 36. FIG. 3b schematically shows the molecular orientation and the principal values of the dielectric tensor of the molecules in LC layer 36 in FIG. 3a.

When an electric field is applied between the two electrodes the LC structure is distorted and the net electro-optical effect is a variation of the phase retardation between the ordinary and extraordinary waves. With strong anchoring where the LC molecules orientations on the surfaces are fixed, the LC director profile becomes non-uniform along the normal to the substrate z-axis, when a voltage V is applied. For example for uniformly aligned LCD (anti-parallel alignment) the director profile is shown in FIG. 3c, which contains graphs showing the profiles of the tilt angle in response to an applied voltage calculated for LC E44 of Merck at different voltages as indicated on the graphs. The calculation assumes nearly fixed molecules at the boundaries with small pretilt. The total retardation should then be calculated from the integral:

$$\Gamma = \frac{2\pi}{\lambda} \int_0^d [n_e(\theta(V,z)) - n_o]dz \quad (1)$$

where $\lambda$ is the wavelength in vacuum, $n_e$ is the extraordinary index of refraction which depends on the molecule tilt angle $\theta$, $n_o$ is the ordinary index of refraction equals to the refractive index perpendicular to the molecules axis $n_\perp$, and d is the LC layer thickness.

Upon variation between 0° and 90°, $n_e$ varies from $n_o$ to $n_\parallel$ according to the following relationship:

$$n_e(\theta(V),z) = \frac{n_\parallel n_o}{\sqrt{n_o^2 + (n_\parallel^2 - n_o^2)\sin^2\theta(V,z)}} \quad (2)$$

The dispersion of the LC refractive indices can be calculated based on the Sellmeier type relations:

$$n_{\perp,\parallel} = \sqrt{\frac{A_{\perp,\parallel}\lambda^2 - 1}{B_{\perp,\parallel}\lambda^2 - 1}} \quad (3)$$

as expounded in the article entitled [12]. As an example for the E44 LC material, the constants are given as follows, for the wavelength given in nm:

$A_\perp = 9.8468 \times 10^{-5}$ nm$^{-2}$; $B_\perp = 4.3937 \times 10^{-5}$ nm$^{-2}$;
$A_\parallel = 6.7553 \times 10^{-5}$ nm$^{-2}$; $B_\parallel = 2.3057 \times 10^{-5}$ nm$^{-2}$ The transfer function for a uniformly aligned nematic LCD between two parallel polarizers with the optic axis oriented at 45° with respect to the polarizer axis is $\cos^2(\Gamma/2)$. Similarly, when it is between crossed polarizers, the transfer function is $\sin^2(\Gamma/2)$. For more accurate treatment which takes into account the additional alignment layers, the electrodes layers and other antireflection coatings, the 4×4 propagation matrix approach should be used.

The tilt angle profile $\theta(z)$ depends on the external electric field applied, and it is governed by a nonlinear differential equation which results in a larger angle at the middle of the LC layer compared to the facets at $z=0$ and $z=d$ [13]. FIG. 3c is a simulation showing how the tilt of the molecules (with constant boundary conditions) produces the nonuniform $\theta(z)$ curves for each voltage for the case of anti-parallel fixed boundary conditions. The simulation shows the LC tilt angle $\theta(z)$ as a function of z/d, the coordinate normal to the plates normalized to the LC layer thickness, for normalized voltages in the range: Vr=1-3. If higher voltages were to be used, the LC tilt angle could be made even closer to 90°, but at the expense of the less convenient electrical arrangement.

Similar to the anti-parallel aligned nematic device described above, one can analyze other nematic LC modes known in the existing art such as the vertically aligned and the pi-cell. The anti-parallel aligned LC device has two main disadvantages: low speed when the device becomes thick and strong dependence of the retardation on the incidence angle. Both the vertically aligned device and the pi-cell improve these parameters but they are usually accompanied with lower total retardation. To overcome the problem, in one of the embodiments of the invention that is shown schematically in FIG. 3d, the thick device is split into an assembly of even number of thinner devices. Each pair of devices has the same thickness and the devices in each pair are assembled together so that the directors of the molecules in each device of the pair are a mirror image of those in the other device.

Figure 5:
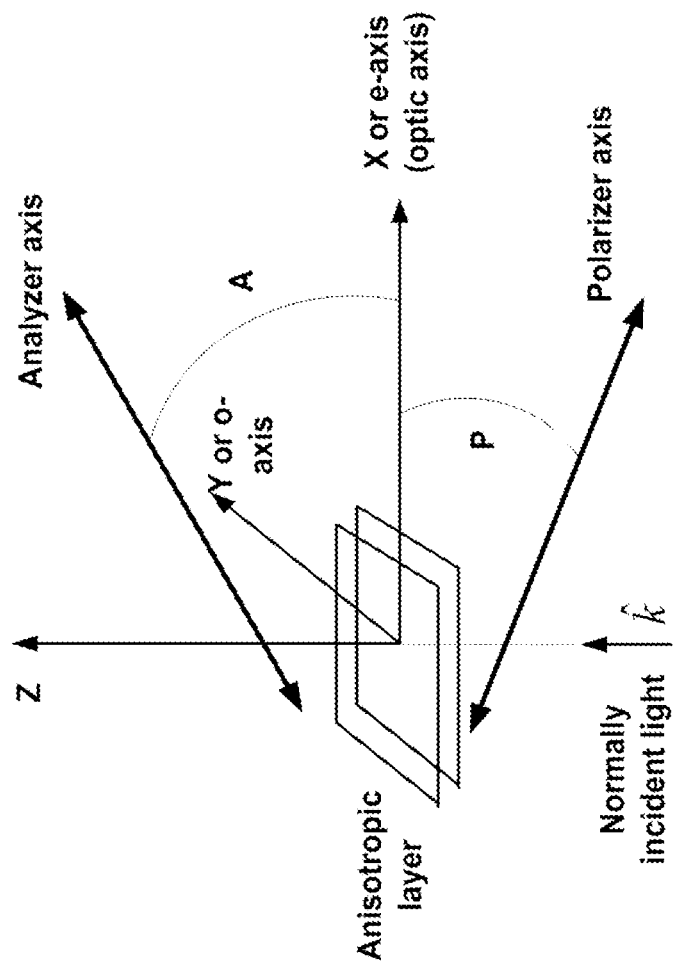
FIG. 5 is a schematic drawing of a birefringent waveplate between two polarizers oriented at arbitrary angles with respect to the optic axis.

To understand the spectral modulation characteristic of a single LC retarder we refer now to FIG. 5 and assume the anisotropic layer is actually the LC layer situated between two polarizers. When the angle P=−A=45 degrees (crossed polarizers), the transfer function is $T_{LCD} = \sin^2(\Gamma/2)$ and when P=A=45 degrees, the transfer function is $T_{LCD} = \cos^2(\Gamma/2)$. Hence the transfer function is composed of a series of transmission peaks which can be tuned (modulated) by changing the voltage. A single LC retarder will be useful in selecting between two or three different wavelengths; however to be able to select between more wavelengths, additional retarders are required. To avoid this problem one of the embodiments of the invention provides a continuous voltage waveform to the retarder so that the retardation varies linearly with time: $\Gamma = G_1 t$ with $G_1$ being a constant of the device, the voltage and the wavelength. Under these conditions then the LCD transmission between parallel polarizers may be written as:

$$T_{LCD} = 0.5 + 0.25\exp(2iG_1 t) + 0.25\exp(-2iG_2 t).$$

The output spectrum through the LCD together with the multilayer stack after reflection from the object is: $S(\lambda) = S_{obj}(\lambda)S_s(\lambda)T_{multi}(\lambda)T_{LCD}(\lambda)$ where $S_s(\lambda)$ is the source spectrum that may include effects of other interfaces in the system and $S_{obj}(\lambda)$ is the object spectrum (reflection, transmission or scattering spectra). If Fourier transform is performed on the measured signal the result is $S_{obj}(\lambda)S_s(\lambda)T_{multi}(\lambda)$. Since $S_s(\lambda)T_{multi}(\lambda)$ is known from a reference measurement, the signal image can be deduced by normalization from the object $S_{obj}(\lambda)$ at all the irradiation wavelengths at once. Other possible processing approaches are possible such as the use of the wavelets transform or the Wiener matrix estimation approach. The LC devices comprising the LCSM unit can be composed of a combination of several LC modes stacked together between polarizers. In the Wiener estimation approach several voltage ranges are applied, the output spectra at each of these voltage ranges are grabbed and processed to reconstruct the spectrum scattered, reflected or transmitted through the object. This scheme is called by the inventor the "spectral modulation parallel approach" (SMPA).

Figure 11:
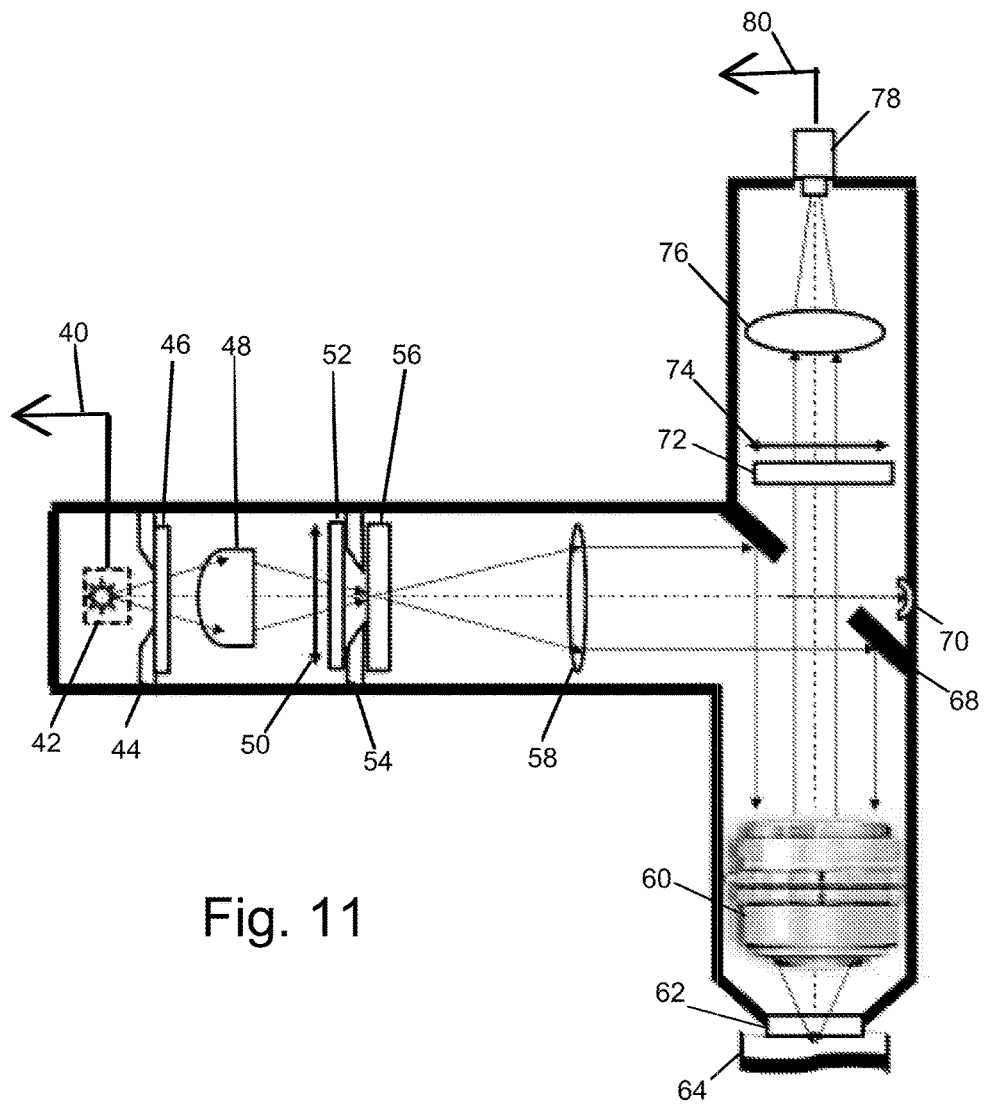
FIG. 11, FIG. 12, FIG. 14, and FIG. 15 schematically show embodiments of imaging modules that comprise the LCD devices used as a source of a series of wide spectral bands and the polarization controller multi-spectral elements that are described herein.
Figure 12:
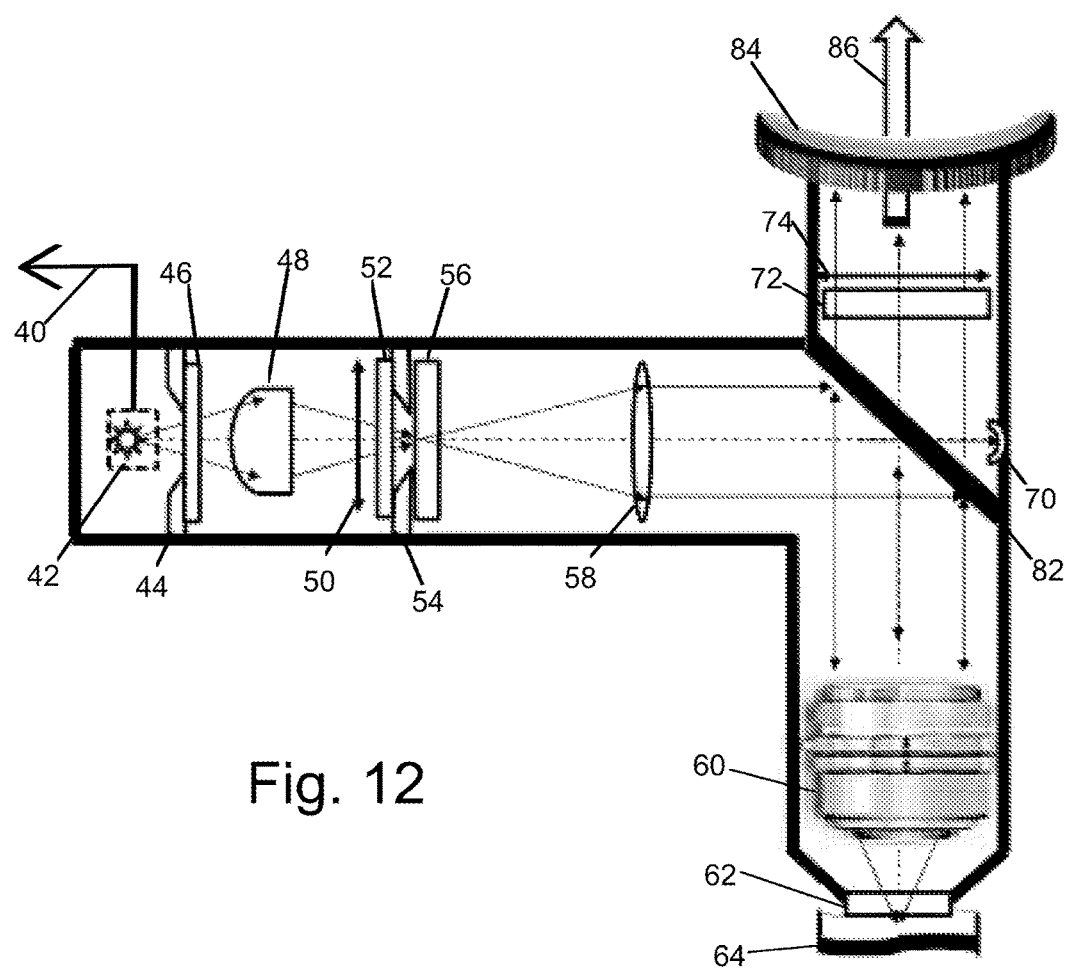

In order to be able to obtain the polarimetric information using the SMPA the two liquid crystal polarization controllers in the imaging system shown for example in FIG. 11 and FIG. 12 are replaced by the switchable achromatic waveplates, the camera chips may be masked with polarization masks or an alternative option is to have multiple cameras, each with an analyzer oriented differently from the others. In order to obtain adequate resolution, a wide range of retardation modulation should be achieved. This means that a retarder with large thickness is required. Since the maximum retardation is given by: $\Gamma_{max} = 2\pi d \Delta n_{mol}/\lambda$ where $\Delta n_{mol} = n_\parallel - n_\perp$ is the molecular birefringence we get the spectral resolution to be: $\delta\lambda = \lambda^2/(d\Delta n_{mol})$. If a high birefringence material with $\Delta n_{mol} = 0.4$ and d=100 microns is used a resolution of 6 nm in the visible range and around 20 nm in the near infrared is obtained. One option to avoid problems due to large thickness is to use an even number of LC devices stacked together whereas each pair of two devices have the same thickness and are oriented in such a way that the directors of their molecules are mirror images of each other (see FIG. 3d). This configuration will improve the angular field of view, the speed and will help producing devices with higher contrast. Another option is to use configurations in which the beam passes twice or several times through the LCD. Faster LC devices can also be used such as the SSFLC mode with fixed boundary conditions.

Figure 4:
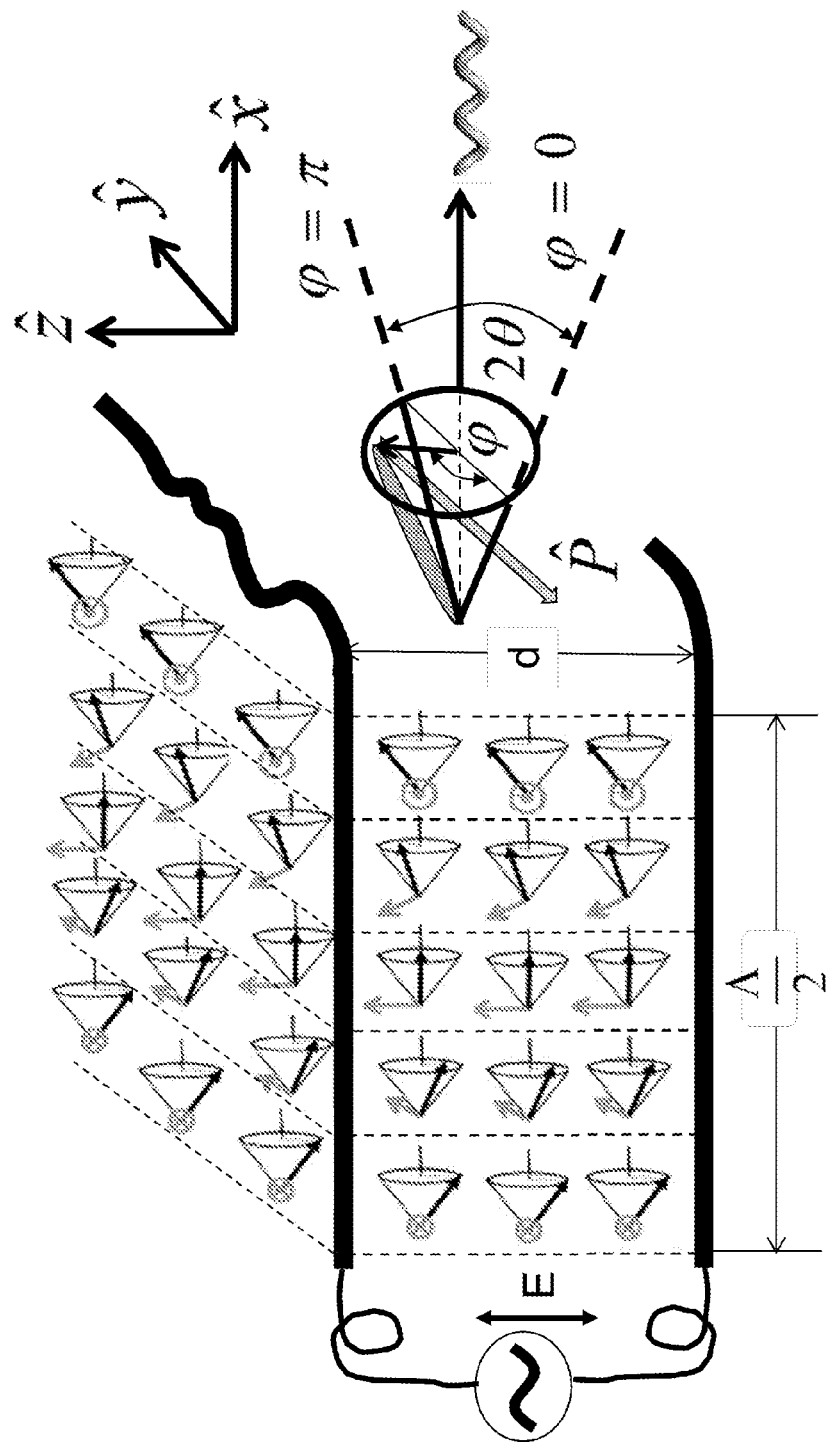
FIG. 4 schematically illustrates the structure of the LC modes of a chiral liquid crystal in the planar geometry between two glass plates.

Case 2: Single Ferroelectric LCD:

The name ferroelectric LCDs (FLCDs) refers to a group of LCDs in which microscopic spontaneous polarization effects are important as an electric field couples strongly to this polarization vector. Among these LCDs are the surface stabilized FLCDs (SSFLCDs), the distorted helix FLCDs (DHFLCDs), the electroclinic LCDs (ELCDs) and the antiferroelectric LCDs (AFLCDs). FIG. 4 schematically illustrates the structures of the LC modes of a chiral liquid crystal in the planar geometry between two glass plates in which the molecules are arranged in layers perpendicular to the substrates and inclined by a tilt angle with respect to the normal to the layers (x-direction). In the chiral smectic C phase the molecules rotate around the normal to the layers as x increases as if they are on the circumference of a cone with tilt angle $2\theta$. Several electrooptic modes arise depending on the ratio between the thickness d to the period of helix $\Lambda$. When $\Lambda \gg d$, the surface anchoring energy causes the helix to unwind, resulting in a uniform structure with all the molecules oriented in one of the two directions: $\varphi=0$ or $\varphi=\pi$.

Applying an electric field along the z direction causes the molecules to switch between these two states. This is called the SSFLC mode, which is known to give binary behavior. When $\Lambda<d$, the helix cannot be unwound by the surface anchoring forces and applying the electric field E causes a distortion of the helix, which can exhibit several electrooptic effects, for examples as tunable diffraction grating, linear retardation and optic axis modulation. This is the DHFLCD mode. The electroclinic effect is associated with chiral smectic A structure in a geometry similar to the SSFLC but because there is no spontaneous ferroelectric polarization, the molecules start to rotate around x-axis continuously and the field changes resulting in a linear electrooptic effect. The present inventor has an extensive experience in devices based on all the liquid crystalline modes [14,15,16].

The most important characteristic of FLCDs is their high speed allowing switching times from tens of microseconds down to few microseconds or less. The electroclinic effect can even allow sub-microseconds switching times. In general the electrooptic effect associated with FLCDs is a rotation of the optic axis direction and no change of the birefringence, however; when the molecules on the boundaries are fixed (strong anchoring), nonuniform structures appear under the application of a small external field resulting in a net change of the birefringence as it was shown by the present inventor [17]. In the DHFLCD case the structure is helicoidal and acting as a subwavelength grating. On the average it acts as a uniaxial medium with the optic axis along the helix. The electrooptic effect associated with the field application is both the rotation of the optic axis and the variation of the birefringence. FIG. 5 is a schematic drawing of a birefringent waveplate between two polarizers oriented at arbitrary angles with respect to the optic axis. The transmission function of a birefringent plate between polarizer and analyzer as shown in FIG. 5 is:

$$T=\cos^2(P-A)-\sin(2P)\sin(2A)\sin^2(\Gamma/2) \quad (4)$$

If the optic axis is rotating with the applied field then both P and A are changing in addition to the variation of the retardation F. The end result is a series of wide transmission peaks.

Figure 6:
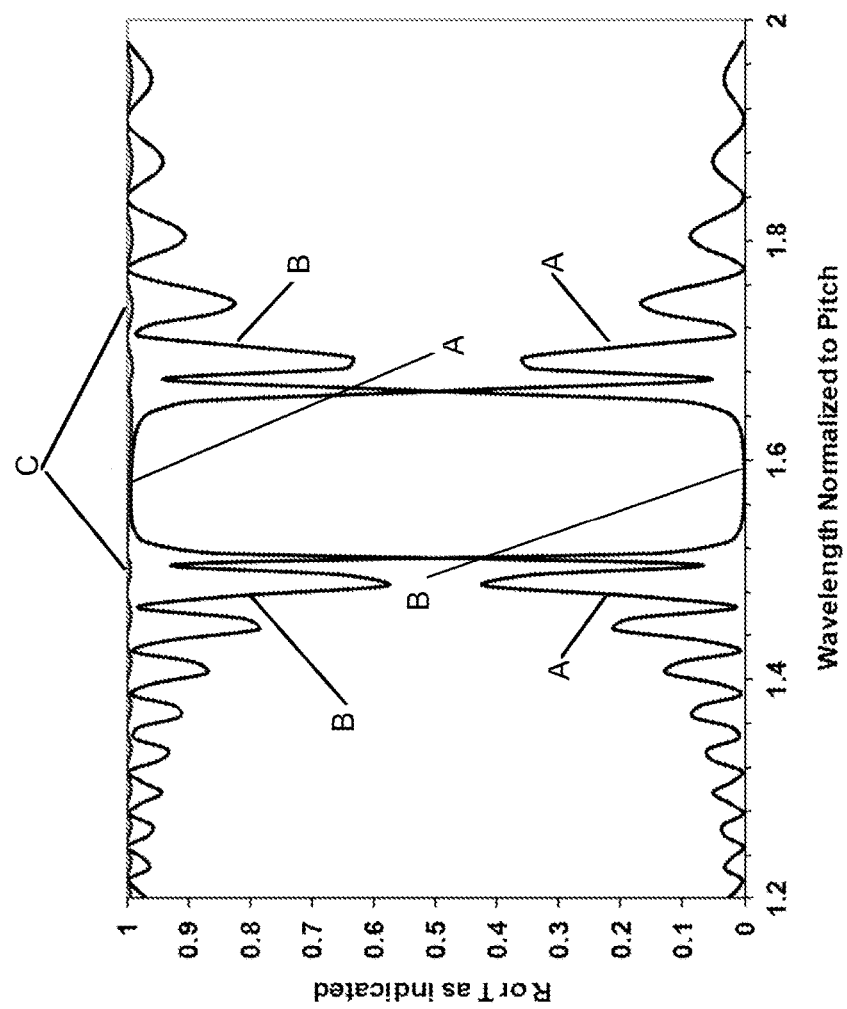
FIG. 6 shows the calculated reflection and transmission spectra of right circularly polarized light from a right handed helical structure of cholesteric LC as well as the transmission of left circular polarization.

Case 3: Single Helical LCD:

Helical LCs are LCs with helicoidal structure that emerges spontaneously as a result of the chirality of the LC molecules. Examples include cholesteric LCs (CLCs), blue phases and the chiral smectic LCs (SCLCs) (The DHFLCD is one of them). Considering the structure in FIG. 4 but with the layers parallel to the substrates so that the helix axis is along the z-direction, a periodic anisotropic stratified structure is obtained. The CLCs structure is optically the same but with $\theta=90°$. Because of their anisotropic periodic structures these LCs exhibit polarized reflection peaks that depend on the period of the structure $\Lambda$, the average refractive index $n_{av}$ and the molecular birefringence $\Delta n=n_e-n_o$. At normal incidence they exhibit a single reflection peak for light that is circularly polarized with the same helicity as the structure while the light with opposite helicity is transmitted without any attenuation. FIG. 6 shows the calculated reflection A and transmission B spectra of right circularly polarized light from a right handed helical structure of cholesteric LC 15 periods thick having n1=n2=1.52, n3=1.65, and $\theta=90$, as well as the transmission of left circular polarization C showing that only the circular polarization with the same helicity as the medium gets reflected. The peak position is given by: $\lambda_{HLC}=\Lambda n_{av}$ and its FWHM is given by: FWHM=$\Lambda\Delta n$ as shown in the example drawn in FIG. 6. For the visible range the period should be around 300 nm in order to get reflection in the visible range $\lambda_{HLC}=\Lambda\Delta n_{av}=300\times1.6=480$ nm, assuming $n_{av}=1.6$. The smallest FWHM will be FWHM=$300\times0.1=30$ nm assuming molecular birefringence of $\Delta n=0.1$. In order to get total reflection for unpolarized light two Helical LC (HLC) structures with opposite helicity can be stacked together. At oblique incidence additional peaks appear with other unique polarization properties. Hence the combination of these band pass tunable filters with the aforementioned multilayer stack gives us a tunable discrete narrow spectral band. The present inventor is an expert on the optics of helicoidal structures in particular helical LCs [18,19,20,21].

Figure 7:
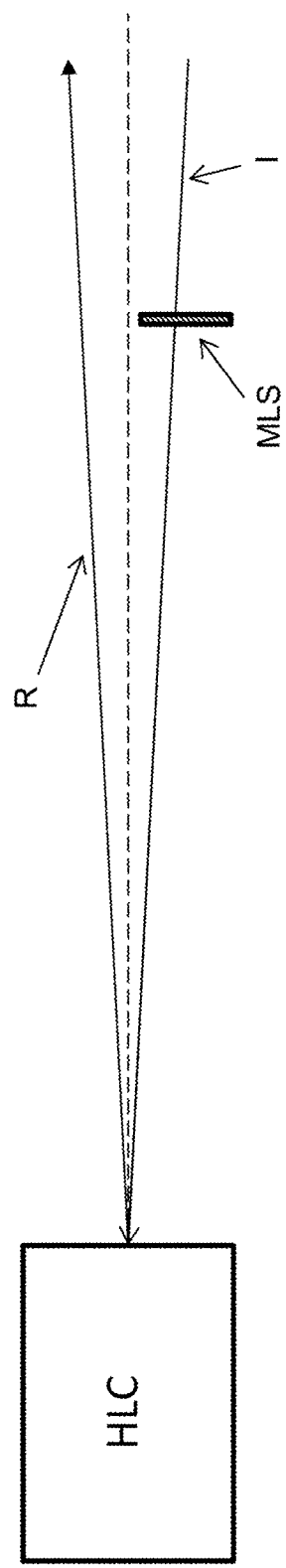
FIG. 7 schematically shows an embodiment of the setup for combining HLCDs with a multilayered structure on a separate substrate in order to obtain narrowband multispectral filtering.

FIG. 7 schematically shows an embodiment of the setup for combining HLCDs with a multilayered structure on a separate substrate in order to obtain narrowband multispectral filtering. The multilayered stack MLS can be inserted in the incident I or reflected R beams path. The HLC can be made from two layers, one right handed and one left handed helix to overcome the polarization dependence. Small incidence angle is preferred to avoid the use of beam splitters yet operating with a single reflection peak. Heating the HLC results in an increase of the helix pitch A and, therefore, to a red shift in the reflection peak. As the HLC reflection peak coincides with one of the transmission peaks of the multilayered structure a narrower peak is obtained. The peak shift with an applied electric field requires an applied field perpendicular to the helix axis, meaning in the substrates plane. This can be achieved with interdigitated electrodes, which means applying high voltages and therefore this embodiment is less preferable in this case. Another embodiment of HLCs involves the use of short pitch (<350 nm) CLC aligned so that the helix axis is in the substrates plane and the thickness of the LC device is much larger than the helix pitch. In this case the structure behaves as a switchable retardation plate with fast speed due to the flexoelectric polarization.

Case 4: Combination of Several LCD Components:

Apart from case 3, all the other cases are mainly suitable for selecting between two (in certain cases three) narrow spectral bands. For a larger number of spectral bands however, the use of additional LCD components is required. The choice of the LCD components depends on the number of spectral bands to be selected, their FWHM and the location of their center wavelengths $\{\lambda_j\}$. The tendency is to minimize the number of components in order to maximize the light throughput and the switching speed. For example for the selection between three different narrow spectral bands two LCD elements are required while for five different spectral narrow band three LCD units are required. Specific examples include the following:

1. Combination of two or three LC retarders each between two polarizers oriented with the optics axis at azimuth angles $P=P_1,P_2,P_3$ and $A=A_1,A_2,A_3$ to the polarizer and analyzer axis having thicknesses $d_1,d_2,d_3$ and made from LC materials with molecular birefringence $\Delta n_1$, $\Delta n_2, \Delta n_3$ respectively. The optical retardations $d_1\Delta n_1$, $d_2\Delta n_2, d_3\Delta n_3$ are selected based on the spectral range, bandwidth and speed required. Usually the thinner the LC layer the higher the speed, hence the tendency is to have it as thin as possible. Different voltages are applied to each retarder in order to compensate for production tolerances concerning deviations from the nominal birefringence and the nominal thickness. Embodiments for operation in the visible and near infrared ranges include but are not limited to the following:

1.1 $P_{1-3}=-A_{1-3}=45°$, $d_2\Delta n_2=1.35 d_1\Delta n_1$, $d_3\Delta n_3=3.6 d_1\Delta n_1$
   1.2 $P_{1-3}=A_{1-3}=45°$, $d_1\Delta n_1=0.49 d_2\Delta n_2=0.26 d_3\Delta n_3$ 1.3 $P_{1,2}=A_{1,2}=45°$, $P_3=-A_3=45°$, $d_1\Delta n_1=0.5d_2\Delta n_2$, $d_3\Delta n_3=0.3d_1\Delta n_1$ 1.4 $P_{1-3}=-A_{1-3}=45°$, $d_1\Delta n_1=0.32d_2\Delta n_2$, $d_3\Delta n_3$, $0.21d_1\Delta n_1$ 2. Combination of several LC retarders N<10 with their optic axis oriented with respect to the polarizer axis by an azimuth angle $\phi_j=(j-1)c+1)P$ with j=1, 2, 3, ... N being the number of the retarder, c is a positive real integer number and P is the polarizer axis direction with respect to the first retarder. The whole stack is assembled between two parallel polarizers and the azimuth of the last retarder has to be odd multiples of $\pi/2$, that is $\phi_N=(2m+1)\pi/2$. The retarders have thicknesses $d_j$ and made from LC materials with molecular birefringence $\Delta n_j$. The optical retardations $d_j\Delta n_j$ are selected based on the spectral range, bandwidth and speed required. Preferred embodiments include but not limited to the following:

2.1 N=9, $\phi_9=\pi/2$, c=1, 2 or 5 and $d_j\Delta n_j=\lambda_{max}$ where $\lambda_{max}$ is the highest center wavelength of the narrow spectral band required within the spectral range of interest.

2.2 N=5, $\phi_5=\pi/2$, c=1, 2 or 5 and $d_j\Delta n_j=2\lambda_{max}$ where $\lambda_{max}$ is the center wavelength of the narrow spectral band with the largest wavelength required within the spectral range of interest.

3. Periodic arrangement of LC retarders between two polarizers such that in each period there are few retarders arranged with respect to each other at a certain fixed azimuth angle. Examples include:

3.1 Each unit cell contains 3 LC retarders twisted with respect to each other by an angle of 60 degrees. The number of periods should preferably be less than 3. The thickness of each retarder is $d=2\lambda_{max}/3(n_o+n_e)$ where $\lambda_{max}$ is the center wavelength of the narrow spectral band with the smallest wavelength required within the spectral range of interest. The polarizer and analyzer axes are at an angle of 60 degrees with respect to the optic axis of the first retarder.

3.2 Each unit cell contains 4 LC retarders twisted with respect to each other by an angle of 45 degrees. The number of periods should preferably be less than 3. The thickness of each retarder is $d=\lambda_{max}/2(n_o+n_e)$ where $\lambda_{max}$ is the center wavelength of the narrow spectral band with the largest wavelength required within the spectral range of interest. The polarizer and analyzer axes are at an angle −45 degrees with respect to the optic axis of the first retarder.

3.3 Each unit cell contains 2 LC retarders twisted with respect to each other by an angle of 90 degrees. The number of periods should preferably be less than 3. The thickness of each retarder is $d=2\lambda_{max}/(n_e-n_o)$ or multiples of it where $\lambda_{max}$ is the center wavelength of the narrow spectral band with the largest wavelength required within the spectral range of interest. The polarizer axis and analyzer axes are at an angle −45 degrees with respect to the optic axis of the first retarder.

3.4 Each unit cell contains 2 LC retarders twisted with respect to each other by an angle of 90 degrees. The number of periods should preferably be less than 3. The thickness of each retarder is $d=\lambda_{max}/2(n_e-n_o)$ or odd multiples of it where $\lambda_{max}$ is the center wavelength of the narrow spectral band with the largest wavelength required within the spectral range of interest. The polarizer axis is at an angle 45 degrees with respect to the optic axis of the first retarder and the analyzer is crossed to the polarizer.

Figure 8:
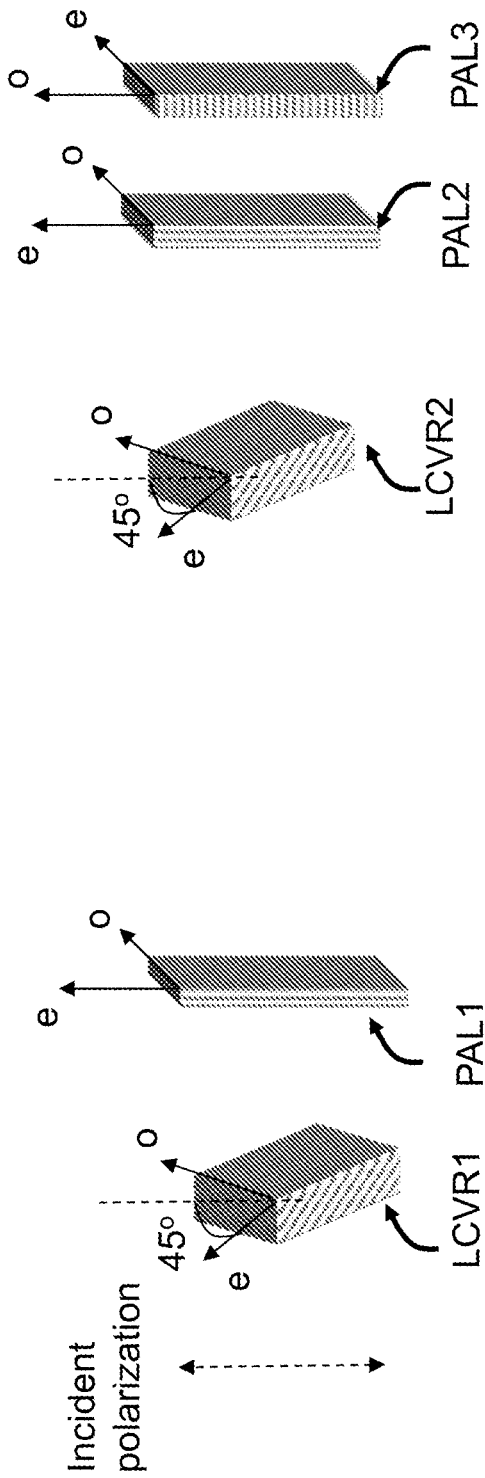
FIG. 8a schematically shows an embodiment of a multispectral polarization rotator comprising a combination of a variable retarder and a passive anisotropic layer.
FIG. 8b schematically shows an embodiment of a multispectral polarization rotator comprising a combination of a variable retarder combined with two passive anisotropic layers having their optic axis oriented at 90 degrees with respect to each other.

Description of the Polarization Controller Multi-Spectral Element:

The continuous multi-spectral polarization controller element is made from one variable LC retarder and one or two passive anisotropic plates. First the case of the use of a single passive anisotropic layer (PAL) as shown in FIG. 8a is considered. Assuming the incident linearly polarized light emitted from the tunable filter is polarized vertically. The LC variable retarder (LCVR) is oriented so that its optic axis makes an angle of 45 degrees with respect to the incident polarization. The PAL1 has its optic axis oriented parallel to the incident polarization. Straightforward calculation shows that when the retardation of the PAL1 is $(2j+1)\pi/2$ with j=0, ±1, ±2, . . . , the combination acts as a polarization controller in which the rotation angle equals half the retardation of the variable retarder. To see this more clearly the Jones matrix for the stack is given by:

$$J = e^{-i\varphi_{av}}\begin{pmatrix} \cos\Gamma/2 & -i\sin\Gamma/2 \\ \sin\Gamma/2 & i\cos\Gamma/2 \end{pmatrix} \quad (5)$$

Where here: $\varphi_{av}$ is a common phase while $\Gamma$ is the retardation of the LCVR. The Jones vector for the incident polarization is described by: $V_{input}=(1,0)^t$. Hence the output Jones vector is: $V_{out}=(\cos\Gamma/2, \sin\Gamma/2)^t$, meaning that the output remains linearly polarized but rotated by an angle equals to $\Gamma/2$ which is controlled by the voltage. The preferred embodiment is to have the PAL1 layer made of a subwavelength dielectric grating deposited on one side of the LCVR for compactness. Subwavelength dielectric gratings with period P<<$\lambda$ and fill factor f act as birefringent plates with their optic axis along the grating vector. Their effective indices up to the $2^{nd}$ order expansion in P/$\lambda$ are:

$$n_{TE2} = n_o = \left\{n_{TE0}^2 + \frac{1}{3}\left[\frac{\pi f(1-f)p}{\lambda}\right]^2(n_g^2-n_m^2)^2\right\}^{1/2} \quad (6)$$

$$n_{TM2} = n_e = \left\{n_{TM0}^2 + \frac{1}{3}\left[\frac{\pi f(1-f)p}{\lambda}\right]^2\left(\frac{1}{n_g^2}-\frac{1}{n_m^2}\right)^2 n_{TM0}^6 n_{TE0}^2\right\}^{1/2} \quad (7)$$

Where here:

$$n_{TE0} = \sqrt{n_m^2(1-f)+fn_g^2}, \text{ and} \quad (8)$$

$$n_{TM0} = \frac{n_m n_g}{\sqrt{n_g^2(1-f)+fn_m^2}}$$

The indices: $n_g$, $n_m$ are the refractive indices of the grating lines (higher index) and spaces (lower index) respectively.

Due to the unique dispersion relations as given in equations (6)-(8), the use of a single subwavelength deep grating to act even as a nearly achromatic retarder is possible. For example using lamellar grating parameters having lines made of material with refractive index of 1.798, period of p=400 nm, fill factor of f=0.7 and height of h=1150 nm gives achromatic phase retardation of $\pi/2$ over the visible and NIR ranges up to 1200 nm. For gratings covered with additional superstrate layer such as the one shown in FIG. 9 it is even possible to get a better achromatic operation for example using the values:

$n_{sup}, n_{sub}=1.798; n_m=1; n_g=1.99; f=0.8; p=400$ nm; $h=1500$ nm.

Figure 9:
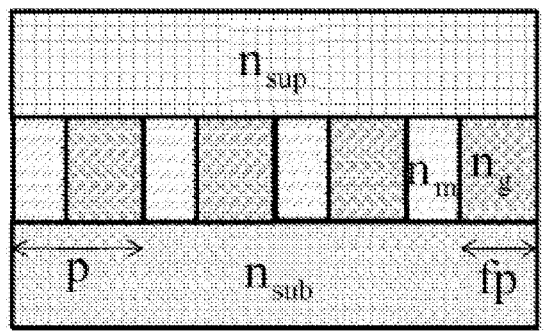
FIG. 9 schematically shows a waveguide and grating covered with an additional superstrate layer.

A subwavelength grating such as that shown in FIG. 9 can act as a uniaxial layer or even achromatic retarder with proper choice of the materials and the geometrical parameters. The line width is the product of the fill factor times the period=fxp. Combination of several subwavelength grating structures is also possible, which will give achromatic retardation at much wider spectral range.

Figure 10:
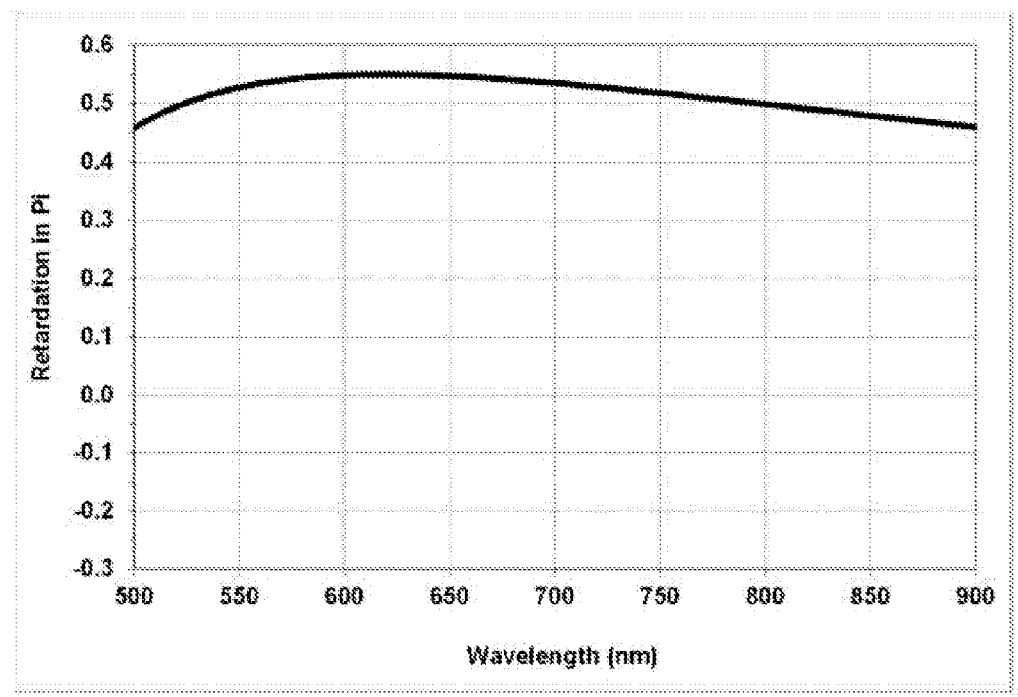
FIG. 10 is a graph showing an example of a nearly achromatic waveplate made of two E44 LC retarders homogenously aligned.

A second embodiment of multi-spectral polarization controller, which is shown in FIG. 8b uses the LCVR with a combination of two PALs having their optic axis oriented perpendicular to each other. The combination PAL1 and PAL2 acts as a nearly achromatic waveplate with a proper choice of their retardation dispersion. The embodiment discussed here comprises two LC retarders in which their retardation is adjusted by a fixed voltage to compensate for variations in the LC thickness. As an example FIG. 10 shows a case where two LC retarders made of two homogeneously aligned nematic LC (Merck E44), each held at different fixed voltage. The two retarders have thicknesses of 46 and 50 microns and are held at two fixed voltages. The figure shows achromatic phase retardation in the range 500-900 nm within 10% around the value of $\pi/2$.

Hence the combination shown in FIG. 8b can operate as a polarization rotator at any wavelength within the range 500-900 nm. That is, it can be used as a polarization rotator even using a continuously tunable filter and not only a multi-spectral tunable filter. This will be of great importance also in the case when color masks are used in front of the cameras instead of using a tunable filter, as discussed herein below. The option of using two subwavelength grating layers made of different materials and different structural parameters instead of two LC retarders is also valid in this case and is preferable in cases where further compact structure is needed. It is even preferable over the use of a single deep subwavelength grating because using two gratings of smaller height is preferable from the point of view of production simplicity. Another example of thin film type anisotropic layers that can be stacked to form PAL1 and PAL2 is the films prepared by the oblique angle deposition technique.

Description of the Multi-Spectral Polarimetric Imaging System:

FIG. 11, FIG. 12, FIG. 14, and FIG. 15 schematically show embodiments of imaging modules that comprise the LCD devices used as a source of a series of wide spectral bands and the polarization controller multi-spectral elements described above. The modules in these figures comprise different combinations of the following elements: Wiring from a light source to a power supply 40; a light source 42; an aperture stop 44; Liquid Crystal Tunable Aperture—LCTA 46; $1^{st}$ lens 48; polarizer 50; Discrete Liquid Crystal tunable filter—DLCTF 52; field stop 54; first Liquid Crystal Polarization Controller—$1^{st}$ LCPC 56; $2^{nd}$ lens 58; objective lens system 60; window 62; sample 64; annular mirror 68; light trap 70; $2^{nd}$ LCPC 72; analyzer 74; $3^{rd}$ lens 76; camera 78; wiring to processor and display 80; beam splitter 82; adapter to digital camera or cellular phone housing 84; collimated light to digital camera lens 86; $1^{st}$ beam splitter 88; and $2^{nd}$ beam splitter 90.

In addition to combining the above mentioned novel devices into one compact design, the design as shown schematically in the configuration for the imaging modules of FIGS. 11, 12, 14, and 15 includes the following novelties:

a. Integrating the DLCTF and $1^{st}$ LCPC elements into the illumination path and locating them in a plane conjugate to the field plane so that uniformity of the wavelength and polarization over the whole field is obtained.

b. Using an annular mirror 68 to split the illuminating beam so that only an annulus of angles is directed towards the objective lens 60 and illuminating the sample 64 symmetrically while letting the scattered light to pass through the central hole of the annular mirror 68 towards a tube lens 76 and camera 78.

c. Locating the $2^{nd}$ LCPC 72 in the imaging path together with a linear analyzer 74 above the splitting mirror 68. This will allow measuring the 9 of Mueller matrix elements of the scattered light $\{M_{ij}\}$ with i,j=1.2.3 in which the incident and output polarization rotators positions span all the orientation combinations: $\{H=0°, V=90°, D=45°, O=-45°\}$. The Mueller matrix connects between the input and output Stokes vectors: $S_{out}=MS_{in}$ and each Mueller matrix element usually represents scattering characteristic of the object being imaged. The input Stokes vector is generated by the polarization state generator PSG composed of the polarizer and $1^{st}$ LCPC. The intensity $I_{out}$ measured by the detector will be determined by $S_{out}=(S_0, S_1, S_2, S_3)$ of the sample and the orientation of the output polarization state analyzer (PSA) which is composed of the $2^{nd}$ LCPC and the analyzer, represented by the Stokes vector $S_A$ so that: $I_{out}=S_A^T M S_{in}$. The Stokes parameters are determined by the intensity $S_0$, the difference between the intensities in the horizontal and vertical polarization directions $S_1=I_H-I_V$, the difference between the intensities at the two diagonal polarization directions D=45 and O=135 degrees: $S_2=I_{45}-I_{135}$ and the difference between the intensities of the right and left circular polarizations: $S_3=I_R-I_L$. The total, linear and circular degrees of polarization are defined by: DOP=$\sqrt{S_1^2+S_2^2+S_3^2}/S_0$; DOLP=$\sqrt{S_1^2+S_2^2}/S_0$; and DOCP=$S_3/S_0$, respectively.

For the other 7 Mueller matrix elements we need to generate in addition right (R) handed or left (L) handed polarizations. For this purpose an additional LC variable retarder will be added to each polarization rotator oriented at 45 degrees to the polarizer or analyzer axis. This additional retarder will be kept at the full waveplate condition for each wavelength but switched to become a quarter waveplate when the R or L polarizations are desired (incident polarization is vertical or horizontal respectively). Alternatively when the achromatic quarter waveplate is made of two LC retarders (the combination PAL1 and PAL2 or PAL3 with PAL4), they will be switched to act as full wave plate (as it is demonstrated in FIG. 16) and then the first LC variable retarder (LCVR1 or LCVR2) will generate the R and L polarizations. The Mueller matrix elements are determined by the 16 combinations shown in the table below:

$$M = \begin{pmatrix} HH+HV+VH+VV & HH+HV-VH-VV & 2DH+2DV-M_{11} & 2RH+2RV-M_{11} \\ HH-HV+VH-VV & HH-HV-VH+VV & 2DH-2DV-M_{21} & 2RH-2RV-M_{21} \\ 2HD+2VD-M_{11} & 2HD-2VD-M_{12} & 4DD-2DH-2DV-M_{31} & 4RD-2RH-2RV-M_{31} \\ 2HR+2VR-M_{11} & 2HR-2VR-M_{12} & 4DR-2DH-2DV-M_{41} & 4RR-2RH-2RV-M_{41} \end{pmatrix} \quad (9)$$

The notations HH for example represent the intensity measured by the detector when the input and output polarizations are horizontal and similarly for the other notations where the first letter represents the incident polarization state and the $2^{nd}$ letter represents the orientation of the polarization state analyzer (PSA). For example the term HH can be shown easily to be obtained by setting: $S_{in}^T = S_A^T = (1,1,0,0)^T$.

d. Using a telecentric design in order to avoid magnification variation and image asymmetry with defocus. This will be achieved by imaging the aperture stop 44 into the exit back focal plane of the microscope objective 60.

e. Locating a tunable aperture 46 preferably made of an annular liquid crystal spatial light modulator at the aperture stop 44 to select the size of the illuminating cone of light within the possible range of the annular mirror 68.

The embodiment for the imaging modality that is shown in FIG. 12 differs from that in FIG. 11 in that there is no $3^{rd}$ lens 76 or camera 78. Instead an adapter 84 is included in order to fit the module into a digital camera or cellular phone using the camera lens instead of the $3^{rd}$ lens 76. A built in zoom of the digital camera can then be used to vary the magnification.

Figure 13:
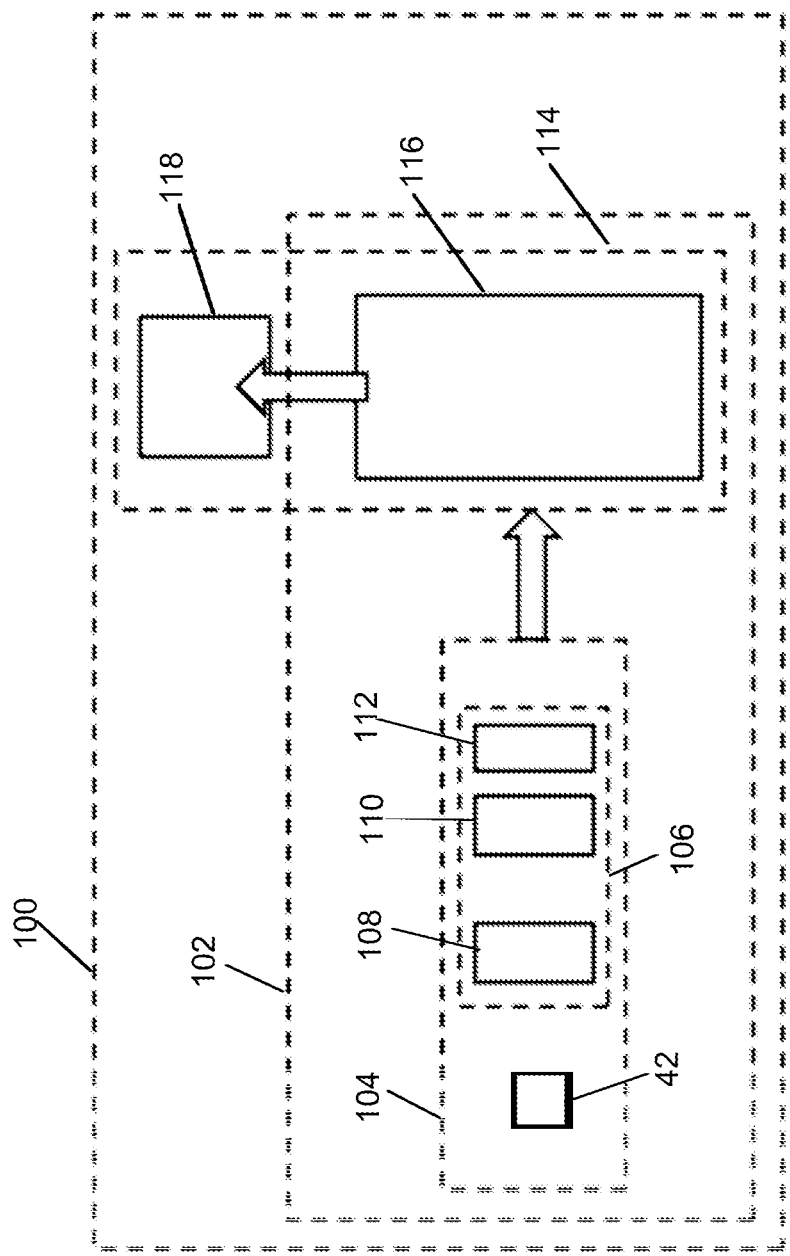
FIG. 13 schematically shows how the elements of the multi-spectral polarimetric imaging systems of the invention described herein can be separated into several smaller units that can be reassembled in different ways.

FIG. 13 schematically shows how the elements of the multi-spectral polarimetric imaging systems 100 of the invention described herein can be separated into several smaller units that can be reassembled in different ways to provide many different products for different applications. Seen in FIG. 13 are the following: LC spectral polarimetric unit 106 comprises LC tunable aperture unit 108, LC tunable filter unit 110, and LC polarization control unit 112. Multispectral polarimetric illuminator unit 104 comprises a light source 42 and LC spectral polarimetric unit 106. Multispectral polarimetric unit 102 comprises multi-spectral polarimetric illuminator unit 104 and unit 116, which comprises an annular mirror or beam splitter, objective lens and a LC polarization control unit. Imaging path unit 114 comprises unit 116 and unit 118, which comprises a projection lens and camera. Unit 118 may contain additional lenses to image the back aperture plane of the objective lens into a plane before the camera in where a $2^{nd}$ LCTA can be located to provide phase or amplitude masks that improve the depth of field or the resolution. One methodology for improving the depth of field is using an annular LCTA, generating several masks and time multiplex them together as described in a previous invention originating from the research group of the present inventor [23]. It should also be mentioned that the use of annulus of rays by itself increases the depth of field.

Examples of some of the products that can be formed from the units described in FIG. 13 are:

1. A set of LC devices including tunable aperture unit 108, tunable filter unit 110 (or a spectral modulation unit) and polarization control unit 112 are used either separately or assembled either two together or all the three together to function for incorporation into imaging systems and converting them into spectropolarimetric systems.
2. The illuminator unit 104 including the light source and the LC spectral polarimetric unit 106 together with the apertures and condensing and collimation lenses can form an independent unit sold separately as a multi-spectral polarimetric illuminator.
3. The illuminator unit 104 together with the objective lens can be sold with a proper adaptor and software to integrate into existing imaging systems.
4. The whole system 100 can form a multi-spectral polarimetric imaging system.
5. Variety of applications can be developed such as:
    a. Cancer detection (skin, cervical, thyroid)
    b. Retinal imaging (Oxygen mapping)
    c. Pathology
    d. Remote sensing
    e. Food industry inspection (meat freshness, type of meat)

These applications are based on signatures based on the spectral response, the polarimetric response or the combination (spectropolarimetric). For example the spectral response signature can originate from the fact that certain parts of the sample absorb or reflect differently. For example, color, relative chromaticity and their variations and granularity over the image can be correlated with the cancer tissue and its type. Since the reflectance spectrum of normal skin tissue show a minimum in the range 450-650 nm (around 550 nm), which disappears as the tissue becomes malignant, then more wavelengths will be used in this range in order to retrieve the maximum information. The DLCTF described in this invention is suitable for this, because its transfer function contains denser peaks in the range 450-650 nm than at the longer wavelengths range. The ratio between images at 550 nm and at wavelengths outside this minimum range (for example 600-650 nm) will reveal a good indicator for the existence of cancer. Larger wavelengths in the near infrared penetrate deeper in the tissue and allow observing deeper lesions. Similarly polarimetric response signature can originate from the fact that collagen fibers changed their order and anisotropy in the cancer tissue. Mueller matrix elements, Stokes parameters, DOP, DOLP, DOCP and their variations over the image are suitable diagnostic parameters for cancer. For skin cancer the standard well known ABCDE parameters (asymmetry, border, color, diameter and evolution) used today by dermatologists can also be extracted from the images. Instead of the border it is preferable to calculate the fractal dimension of the lesion. Directionality in the skin mole image is another important parameter that is preferable to extract for cancer diagnosis. It represents the existence and some orientational radial order of filament patterns in the image which are indicators of melanoma. This property cannot be seen by the dermatologists. The local contrast and its uniformity is another important parameter for diagnosing cancer tissue from normal tissue. Another group of parameters obtained from combinations of the Mueller matrix elements are of particular interest: $\alpha = (m_{22} + m_{33})$; $\beta = (m_{22} - m_{33})$; $\gamma = \alpha^2 + \beta^2$; $\chi = \alpha\gamma/(\alpha^2 + \gamma^2)$. Since the parameters $\alpha$, $\beta$ are related to the diagonal elements, they are correlated with the depolarization properties. For highly depolarizing media for example $\alpha \approx 0$ and it increases as the depolarization decreases. For example when small dense organelles exist in the tissue such as when cancer exists, the scattering increases and therefore the depolarization and the parameter $\alpha$ increases. The parameter $\chi$ is correlated with the anisotropy degree of the structure for example the degree of order of the collagen fibers in skin tissue. Hence one expects $\chi$ to be larger while $\alpha$ is smaller for healthy skin tissue than for abnormal tissue. These behaviors are wavelength dependent which is why measurements at many wavelengths is required. For example for cancer tissue particularly cervical and thyroid, when the wavelength increases then both parameters $\alpha$, $\chi$ increase because the penetration depth increases.

Figure 14:
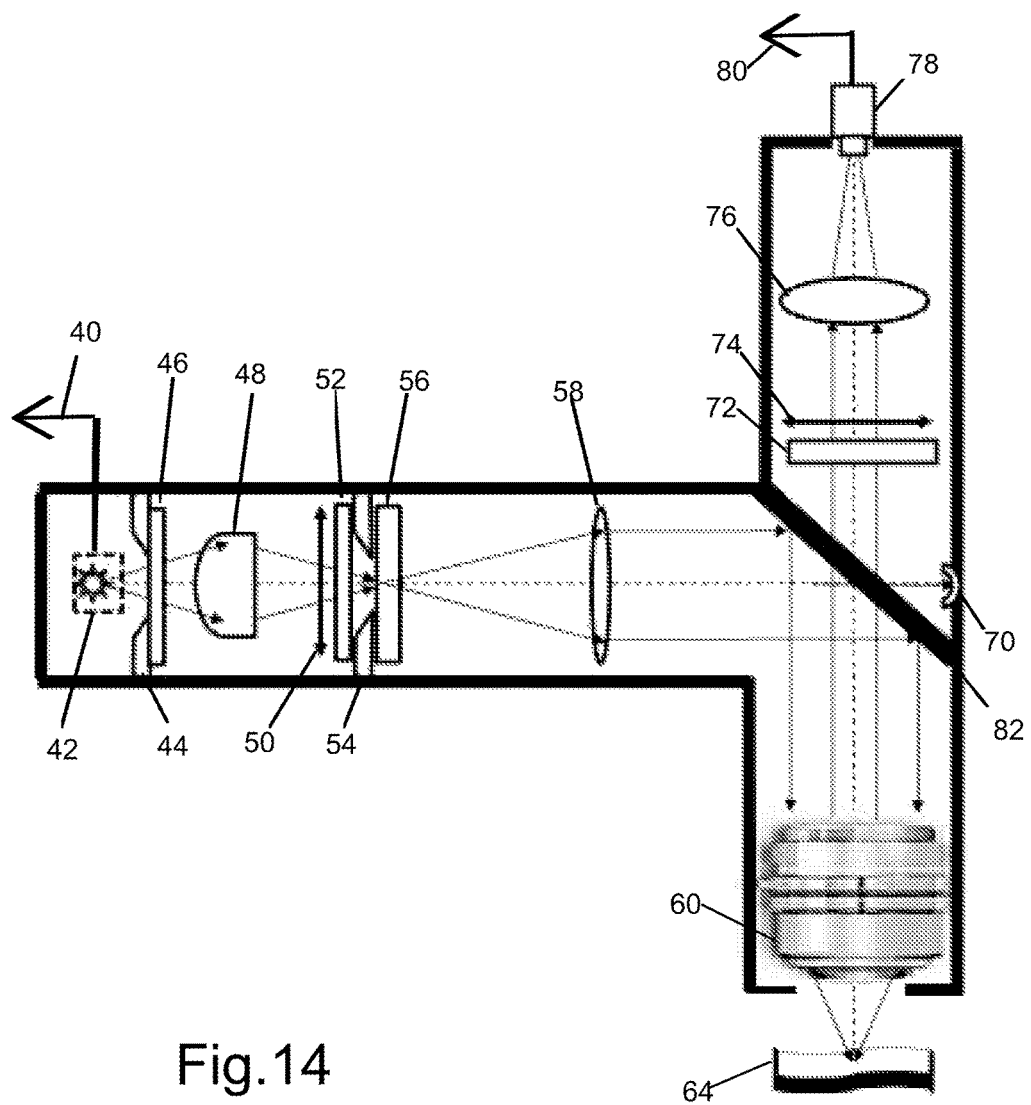

Another important application is in thin films characterization similar to ellipsometry. The system proposed in this invention can measure Stokes parameters, from which the ellipsometric parameters of a multilayered structure or anisotropic material can be measured. For example the azimuth angle of the ellipse is given by: AZ=0.5 arctan $(S_2/S_1)$ and its ellipticity is: ELL=0.5 arcsin $(S_3/\sqrt{S_1^2+S_2^2+S_3^2})$. Hence the system can be used as ellipsometer as well for materials and surfaces characterization, monitoring fabrication processes of semiconductors such as critical dimension measurement and layers overlay misregistration. However in most of the cases for this particular application the specimen is mainly specularly reflected and only very little scattering exists. To measure specular reflection then for these cases, the annular mirror 68 is replaced with a regular beam splitter 82 as shown in FIG. 14. Note also that the window 62 between the objective lens 60 and sample 64, which is important for tissue imaging is removed in this case.

Another embodiment of this invention uses multiple cameras, for example 3, with an analyzer in front of each one oriented at a different orientation to minimize the number of polarization states that each LCPC needs to scan.

Figure 15:
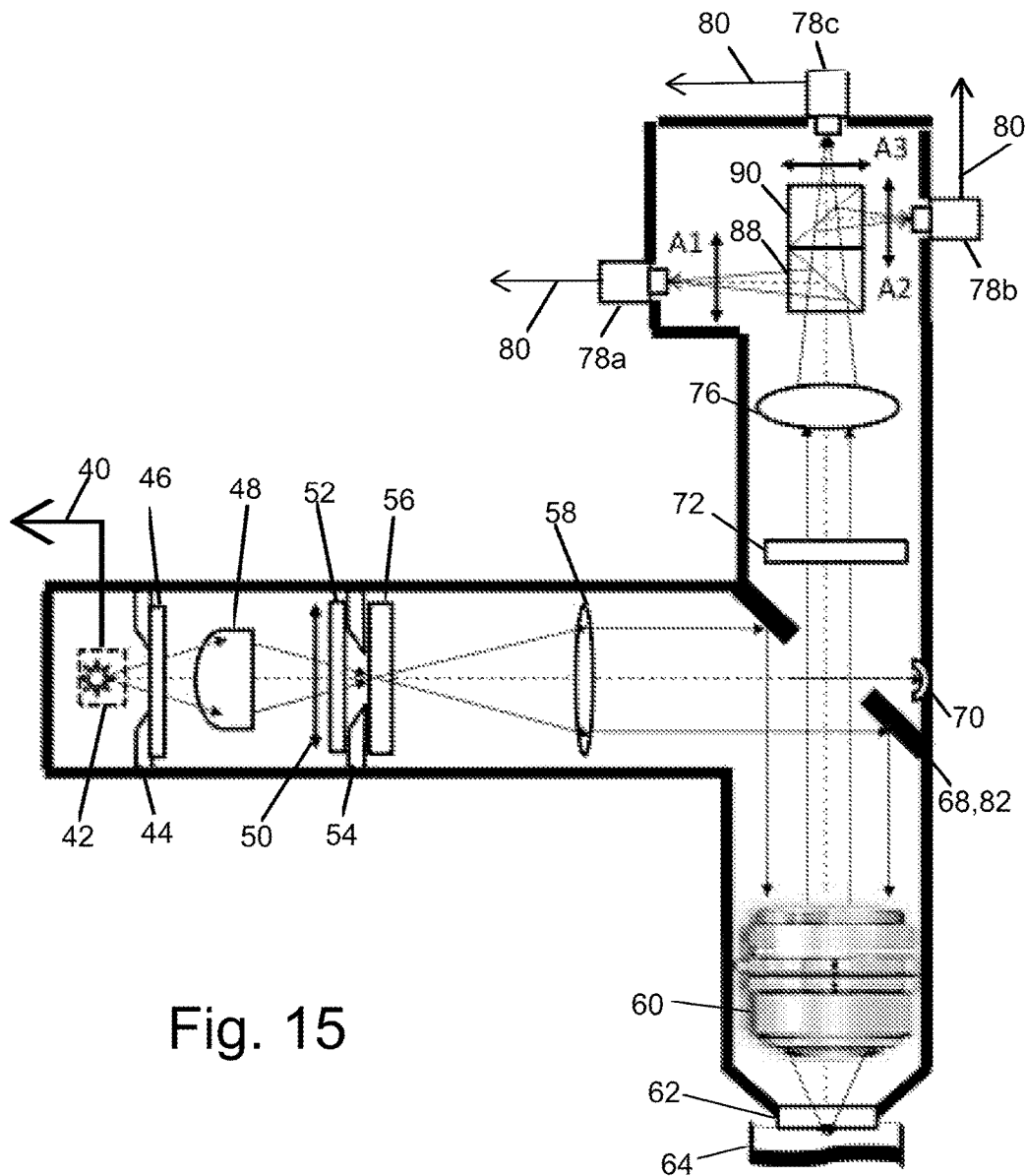

A schematic of this embodiment is shown in FIG. 15. In this embodiment the beam after the projection lens 76 is split into three channels using beam splitters 88, 90. In each channel an analyzer A1, A2, A3 and camera 78a, 78b, 78c are located. The orientation of each analyzer is different from each of the others. A preferable combination of the orientation of the analyzers is (H, V, D) however other configurations are possible such as (H, 60°, 120°). Using these latter orientations, the first three Stokes parameters can be expressed as: $S_0=2(I_H+I_{60}+I_{120})/3$; $S_1=2(2I_H-I_{60}-I_{120})/3$; $S_2=2(I_{60}-I_{120})/\sqrt{3}$. The splitting ration of the $1^{st}$ beam splitter R/T is preferably 1:2 while for the $2^{nd}$ beam splitter R/T is 1:1. The $2^{nd}$ beam splitter can also be a polarizing beam splitter if the first analyzer is chosen at the D orientation. In this case there is no need for the analyzers A2 and A3. The number of polarization states that the LCPCs need to scan with this configuration is smaller by at least a factor of ×3.

Another option to speed up the polarimetric images grabbing is to use a polarization mask in front of the camera chip or imprinted on the camera chip. Possible configurations could be the well-known four pixel configuration (H, V, D, O) or it is also possible with (H, 60, 120) as described above.

Figure 16:
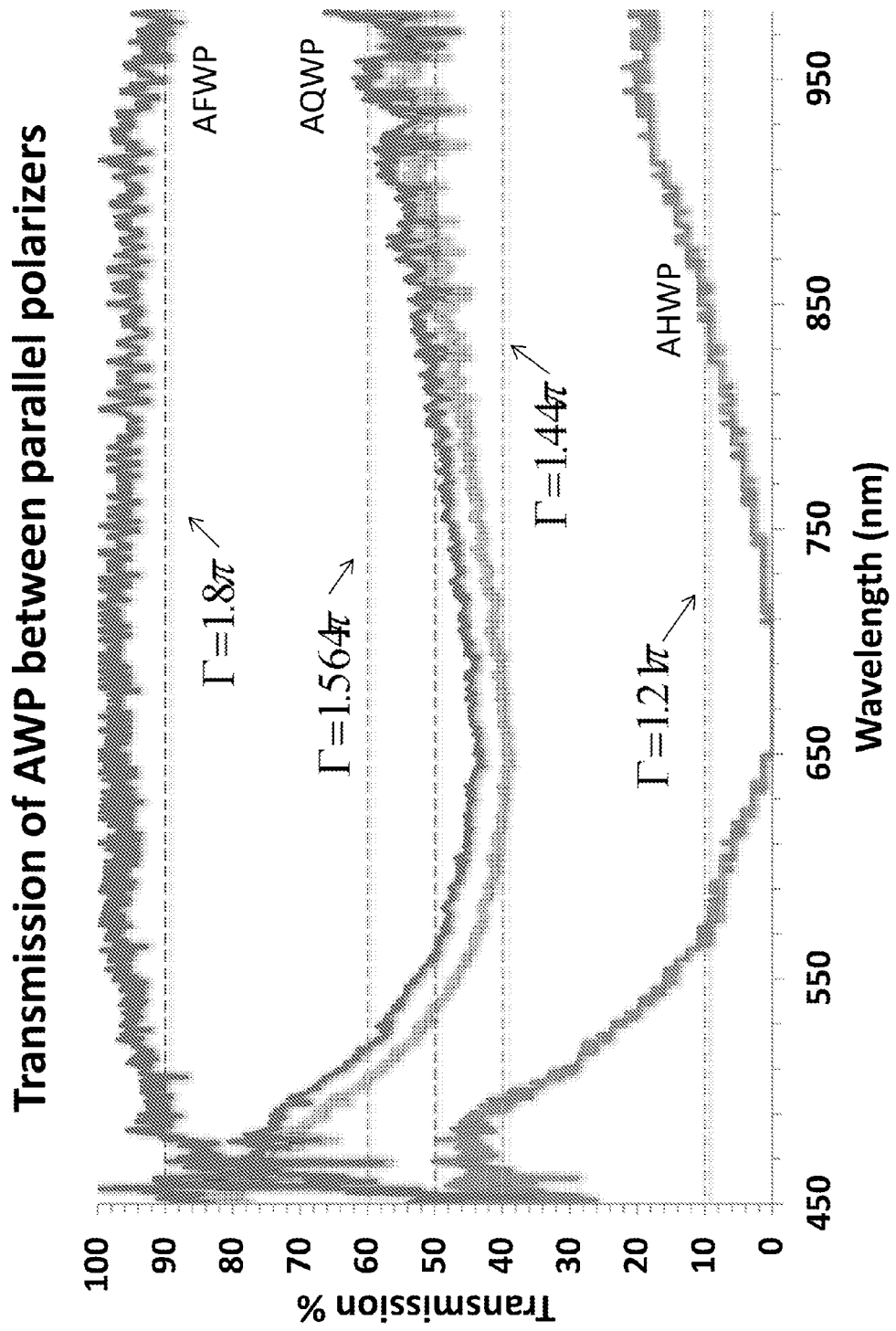
FIG. 16 shows the transmission of tunable achromatic LC waveplate made of two LC retarders under different voltages demonstrating switching between AQWP, AHWP and FWP in the spectral range 500-900 nm.

FIG. 16 shows the transmission of tunable achromatic LC waveplate made of two LC retarders under different voltages demonstrating switching between AQWP, AHWP and FWP in the spectral range 500-900 nm. These results were obtained using as embodiment of the spectropolarimetric imaging system in which the number of liquid crystal devices in the system is minimized. In this configuration multiple cameras are used as in FIG. 15; however an additional color mask is positioned on the chip of each camera. Assuming a pixelated mask made of rectangular pixels divided periodically into unit cells each containing J×K pixels each having different transmission functions centered at different wavelengths. Then a number of spectral images equals to JK will be grabbed in parallel. Since existing technologies provide pixels of size around 3 µm or smaller, then a reasonable number of pixels in a unit cell is 3×3 without sacrificing the resolution significantly for many applications. In this configuration there will be no need for the DLCTF 52, hence improving the speed and making the system more compact. Another method to obtain the colored pixels is to create thin film coatings on the camera pixels directly; however making JK lithographic steps on an existing camera chip is not feasible. The solution proposed in this invention of making the color mask on a glass plate that can be fitted on top of the camera chip is more realistic and provides a cheaper solution. Since no LCTF is used in this configuration, in order to vary the polarization state the LCPCs 56, 72 have to be achromatic. Since this is not possible for all the polarization states, the inventor proposes the use of a liquid crystal achromatic waveplate made of two LC retarders as disclosed recently in another patent application of the inventor [22]. This waveplate uses two LC retarders oriented at 90 degrees with respect to each other and different voltages applied to them. FIG. 16 shows the possibility of switching between achromatic quarter waveplate (AQWP), half wave plate (AHWP) and full waveplate (AFWP) using the same device. Other achromatic phase shifts are possible using this configuration. Hence using this device both in the input and the output of the system in FIG. 15 will allow scanning a large number of achromatic polarization states. Combined with the color mask on each camera a fast spectropolarimetric imaging system is obtained.

It should be mentioned that the configurations of the spectropolarimetric imaging system described herein can be easily manifested also in the less preferable configuration of oblique non symmetric illumination. The number of cameras that can be used is not limited to only one camera or three cameras, but other configuration of using two or four cameras are also possible and can be easily manifested in the configurations presented herein. In addition optical spectroscopic modules such as Raman or fluorescence excitation source such as a laser can easily be integrated using a dichroic mirror into the illuminator and the emitted fluorescence or Raman signals can be monitored by incorporating another dichroic mirror before the camera to direct the signal to a spectrometer. The objective lens can be replaced or combined with a Zoom lens, which will enable concentrating on small suspicious areas. Once such a small area is identified, higher magnification is applied and the scattered light is directed—all or part of it—to a spectroscopic system which can measure Raman scattering, fluorescence or simply the scattering spectrum. Moreover the objective lens can be replaced with an interferometric microscope objective such as the Mirau or Michleson (objective with beam splitter) or two objectives such as with the Linnik and the interferometric images are captured at different depths of the tissue, different polarization states and different wavelengths. Obtaining the interferometric images at many wavelengths can be Fourier transformed to give the depth information as with frequency domain optical coherence tomography.

Figure 17:
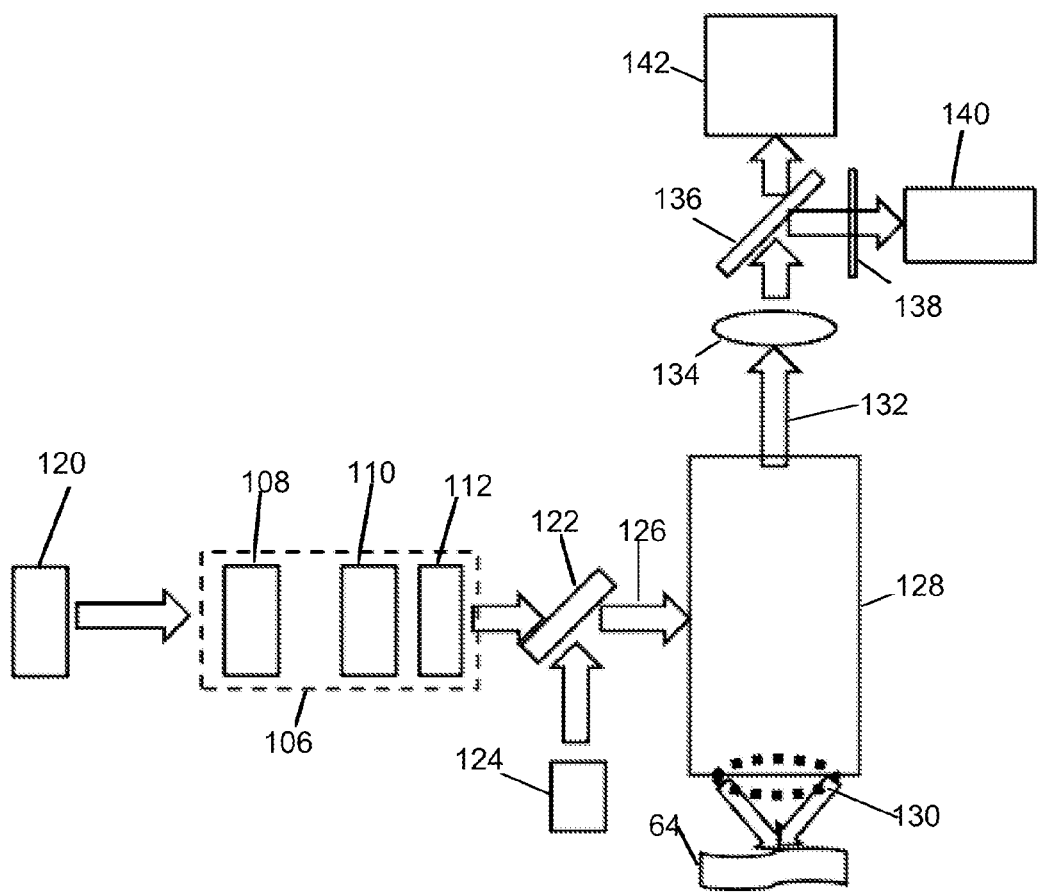
FIG. 17 schematically shows the most general configuration of the spectropolarimetric imaging system of the invention.

The most general system configuration of the spectropolarimetric imaging system of the invention is schematically shown in FIG. 17. Light from a unit 120 comprising a wideband source and illumination optics passes through LC spectral polarimetric unit 106 comprises LC tunable aperture unit 108, LC tunable filter unit 110 or equivalently a spectral modulation unit, and LC polarization control unit 112 to dichroic beam splitter 122. Alternately or together with unit 120 an excitation source 124 can be directed to the dichroic beam splitter 122. The illuminating and/or the exciting beam 126 passes to unit 128, which comprises either a regular or annular beam splitter, an objective lens system (with or without zoom), and a LC control unit. A circularly symmetric tunable annular beam 130 illuminates the sample 64. Scattered or reflected light 132 from sample 64 passes through projection lens 134 to a removable beam splitter 136. If beam splitter 136 is present at least a part of light 132 passes through a removable longpass filter 138 to a spectrometer 140 and part of light 132 passes to image detection unit 142, If beam splitter 136 is not present all of light 132 passes to image detection unit 142, which can comprise one or multiple cameras with analyzers and spectral masks in front.

Although embodiments of the invention have been described by way of illustration, it will be understood that the invention may be carried out with many variations, modifications, and adaptations, without exceeding the scope of the claims.

BIBLIOGRAPHY

[1] U.S. Pat. No. 6,483,580, Y. Xu, I. Abdulhalim.
[2] Kollias N., Stamatas G. N., "Optical non-invasive approaches to diagnosis of skin diseases", *J Investig Dermatol Symp Proc.*, 7, 64-75 (2002).
[3] I. Abdulhalim, R. Moses and R. Sharon, "Biomedical optical applications of liquid crystal devices", *Acta Physica Polonica* A 112 (5) 715-722 (2007).
[4] Avner Safrani, Ofir Aharon, Shahar Mor, Ofer Arnon, Lior Rosenberg and I. Abdulhalim, "Skin biomedical optical imaging system using dual wavelength polarimetric control with liquid crystals", *Journal of Biomedical Optics* 15, 026024-8p (2010).
[5] Ofir Aharon, I. Abdulhalim, Ofer Arnon, Lior Rosenberg, Victor Dyomin, Eldad Silberstein, "Differential optical spectropolarimetric imaging system assisted by liquid crystal devices for skin imaging", *J. Biomedical Optics*, 16(8), 086008-12p (2011).
[6] WO 2012/104784-A1, Ofir Aharon.
[7] Chad A. Lieber and Anita Mahadevan-Jansen, "Development of a handheld Raman microspectrometer for clinical dermatologic applications", *Optics Express* 15 (19), 11874-82 (2007)
[8] Yu. Sinichkin, S. Utz, A. Mavliutov, and H. Pilipenko, "In vivo fluorescence spectroscopy of the human skin: experiments and models", *J. Biomed. Opt.* 3, pp. 201-2111(1998).
[9] Shen-Hao Tseng, Alexander Grant and Anthony J. Durkin, "In vivo determination of skin near-infrared optical properties using diffuse optical spectroscopy", *J. Biomedical Optics*, 13, 014016-1 (2008).
[10] I. Abdulhalim, "Analytic propagation matrix method for linear optics of arbitrary biaxial layered media", *J. Opt. A*, 1 (5), 646-653 (1999).
[11] I. Abdulhalim, "Reflective Polarization Conversion Fabry-Perot Resonator using Omnidirectional Mirror of Periodic Anisotropic Stack", *Optics Commu.* 215, 225-230 (2003).
[12] I. Abdulhalim, "Dispersion relations for liquid crystals using the anisotropic Lorentz model with geometrical effects," I 33, 1027-1041 (2006).
[13] I. Abdulhalim, D. Menashe, "Approximate analytic solutions for the director profile of homogeneously aligned nematic liquid crystals", *Liq. Cryst.* 37, 233-239 (2010).
[14] I. Abdulhalim, G. Moddel, K. M. Johnson, "High Speed Analog Spatial Light Modulator using an a-Si:H Photosensor and an Electroclinic Liquid Crystal", *Appl. Phys. Lett.*, 55, no'16, 1603 (1989);
[15] I. Abdulhalim, G. Moddel, "Optically and Electrically Controlled Light Modulation and Color Switching using Helix Distorsion of Ferroelectric Liquid Crystals", *Mol. Cryst. Liq. Cryst.*, 200, 79(1991);
[16] I. Abdulhalim, "Strong Effect of the Interface Layers on the Electrooptic Response of Ferroelectric Liquid Crystals", *Europhys. Lett.*, 19, 91(1992);
[17] I. Abdulhalim, "Continuous Phase-Only or Amplitude Light Modulation using Ferroelectric Liquid Crystals with Fixed Boundary Orientations", *Optic. Communi.*, 108, 219 (1994)
[18] I. Abdulhalim, L. Benguigui, R. Weil, "Selective Reflection by Helicoidal Liquid Crystals: Results of an Exact Calculations using the 4×4 Characteristic Matrix Method", *J. De Phys.*, 46, 815 (1985);
[19] I. Abdulhalim, "Light Propagation Along the Helix of Chiral Smectics and Twisted Nematics", *Opt. Commun.*, Vol. 64, No. 5, 443 (1987);
[20] I. Abdulhalim, "Unique optical properties of anisotropic helical structures in Fabry-Perot cavity", *Opt. Lett.* 31, 3019-21 (2006);
[21] I. Abdulhalim, "Effect of the number of sublayers on axial optics of anisotropic helical structures", *Appl. Opt.* 47, 3002-3008 (2008)].
[22] U.S. patent application Ser. No. 14/818,443, I. Abdulhalim and M. Abuleil.
[23] WO2015/083162, Iftach Klapp, Asi Solodar and I. Abdulhalim

The invention claimed is:

1. A multi-spectral polarimetric variable optical device comprising a liquid crystal aperture tuning unit (LCTA), at least one liquid crystal polarization controller (LCPC) unit, and one of a liquid crystal tunable filter (LCTF) unit or a liquid crystal spectral modulation (LCSM) unit, the multi-spectral polarimetric variable optical device configurable as a multi-spectral polarimetric imaging system and comprising the following elements:
  a) a light source;
  b) an aperture stop in front of the light source;
  c) a LCTA unit located immediately in front of the aperture stop;
  d) a first lens in front of the LCTA unit;
  e) a polarizer in front of the first lens;
  f) an LCTF unit or LCSM unit in front of the polarizer;
  g) a field stop immediately in front of the LCTF unit;
  h) a first LCPC unit immediately in front of the field stop;
  i) a second lens in front of the first LCPC unit;
  j) an annular mirror oriented at 45 degrees to the light from the light source that passes through elements "b" to "i";
  k) a light trap that absorbs light from the light source that passes through the open center of the annular mirror;
  l) an objective lens that receives light reflected by the annular mirror;
  m) a window through which light focused by the objective lens passes;
  n) a sample on which the objective lens focuses the light;
  o) a second LCPC unit, which receives light that is reflected by or scattered from the surface of the sample and passes through the window, the objective lens, and the open center of the annular mirror;
  p) an analyzer in front of the second LCPC unit;
  q) a third lens in front of the analyzer; and
  r) a digital camera onto which the third lens focuses the light reflected or scattered from the surface of the sample, said camera is capable of zooming to vary magnification.

2. The multi-spectral polarimetric imaging system of claim 1, wherein elements "a)" to "r)" are separated into several smaller units that are reassembled in different ways to provide many different products for different applications.

3. The multi-spectral polarimetric imaging system of claim 1, wherein the third lens (element "q)") and the camera (element "r)") are replaced by an adapter configurable to fit the imaging module into a digital camera or cellular phone.

4. The multi-spectral polarimetric imaging system of claim 1, wherein the analyzer and camera are replaceable by at least one beam splitter placed after the third lens, wherein the beam splitters divide the light passing through the third lens into at least two channels each of which comprises an analyzer and a camera, wherein the orientation of each analyzer is different from the orientation of each of the others.

5. The multi-spectral polarimetric imaging system of claim 4, wherein the number of beam splitters is two and the number of analyzers and cameras is three.

6. The multi-spectral polarimetric imaging system of claim 1, comprising a color mask on a glass plate fitted on top of the digital cameras sensor chip, wherein the imaging system does not comprise a LCTF unit and each of the first and second LCPC units is replaceable by two or more LC retarders oriented at different angles with respect to each other with different voltages applied to each of them to act as tunable achromatic waveplates.

7. The multi-spectral polarimetric imaging system of claim 1, comprising a polarization mask on a glass plate fitted on top of the digital cameras sensor chip, wherein the imaging system does not comprise analyzers.

8. The multi-spectral polarimetric imaging system of claim 1, wherein the LCTF unit is replaced with a LCSM unit and each of the first and second LCPC units is replaced with a tunable achromatic waveplate.

9. The multi-spectral polarimetric imaging system of claim 8, in which the liquid crystal spectral modulation (LCSM) unit is placed in between the annular or regular beam splitter and the objective lens so that double pass is achieved.

10. The multi-spectral polarimetric imaging system of claim 1, in which the objective lens is replaceable with an interferometric microscope objective and beam splitter, as in the Mirau or Michleson interferometer, or with two objectives, as in the Linnik interferrometer, and the imaging system is configurable to capture the interferometric images at different depths of the sample, different polarization states and different wavelengths.

11. The multi-spectral polarimetric imaging system of claim 1 combined with a spectroscopic system, which is capable of measuring the scattering spectrum, Raman scattering, or fluorescence, wherein once a small area in the sample is identified, higher magnification is applied and all or part of the scattered light is directed to the spectroscopic system.

* * * * *